United States Patent
Abdi

(10) Patent No.: US 10,898,581 B2
(45) Date of Patent: Jan. 26, 2021

(54) TARGETED DELIVERY OF IMMUNOREGULATORY DRUGS

(71) Applicant: The Brigham and Women's Hospital, Inc., Boston, MA (US)

(72) Inventor: Reza Abdi, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 278 days.

(21) Appl. No.: 15/111,563

(22) PCT Filed: Jan. 9, 2015

(86) PCT No.: PCT/US2015/010851
§ 371 (c)(1),
(2) Date: Jul. 14, 2016

(87) PCT Pub. No.: WO2015/108783
PCT Pub. Date: Jul. 23, 2015

(65) Prior Publication Data
US 2016/0331843 A1 Nov. 17, 2016

Related U.S. Application Data

(60) Provisional application No. 61/928,231, filed on Jan. 16, 2014.

(51) Int. Cl.
| | | |
|---|---|---|
| *A61K 39/395* | (2006.01) | |
| *C07K 16/00* | (2006.01) | |
| *C07K 16/46* | (2006.01) | |
| *C07K 16/28* | (2006.01) | |
| *C07K 16/24* | (2006.01) | |
| *A61K 47/68* | (2017.01) | |
| *A61K 31/436* | (2006.01) | |
| *A61K 47/69* | (2017.01) | |

(52) U.S. Cl.
CPC ........ *A61K 47/6849* (2017.08); *A61K 31/436* (2013.01); *A61K 47/6803* (2017.08); *A61K 47/6927* (2017.08); *A61K 47/6937* (2017.08)

(58) Field of Classification Search
None
See application file for complete search history.

(56) References Cited

U.S. PATENT DOCUMENTS

| | | | |
|---|---|---|---|
| 5,145,684 A | 9/1992 | Liversidge et al. | |
| 5,262,176 A | 11/1993 | Ogawa et al. | |
| 5,489,441 A | 2/1996 | Dwyer et al. | |
| 5,492,814 A | 2/1996 | Weissleder | |
| 6,270,806 B1 | 8/2001 | Liversidge et al. | |
| 7,291,598 B2 | 11/2007 | Sung et al. | |
| 7,348,030 B1 | 3/2008 | Sung et al. | |
| 2003/0157023 A1* | 8/2003 | Roessling | A61K 49/223 424/9.52 |
| 2005/0042298 A1* | 2/2005 | Pardridge | A61K 9/5153 424/489 |
| 2007/0036729 A1* | 2/2007 | Briel | A61B 5/0515 424/9.34 |
| 2009/0186073 A1 | 7/2009 | Yamazaki et al. | |
| 2010/0034874 A1* | 2/2010 | Hirai | A61K 9/127 424/450 |
| 2010/0303723 A1* | 12/2010 | Farokhzad | A61K 47/68 424/9.1 |
| 2011/0045060 A1* | 2/2011 | Ohhashi | A61K 47/42 424/450 |

FOREIGN PATENT DOCUMENTS

| | | |
|---|---|---|
| WO | WO 00/61191 | 10/2000 |
| WO | WO 2008/109483 | 9/2008 |
| WO | 2008/147456 | 12/2008 |
| WO | 2014/008375 | 1/2014 |

OTHER PUBLICATIONS

Morachis et al. Physical and Chemical Strategies for Therapeutic Delivery by Using Polymeric Nanoparticles. Pharmacol Rev 64: 505-519, 2012. (Year: 2012).*
Luo et al. LyP-1-conjugated nanoparticles for targeting drug delivery to lymphatic metastatic tumors. International Journal of Pharmaceutics 385 (2010) 150-156. (Year: 2010).*
Lin et al. Adhesion of Antibody-Functionalized Polymersomes. Langmuir 2006, 22, 3975-3979 (Year: 2006).*
Ishii et al. Treatment of cerebral ischemia-reperfusion injury with PEGylated liposomes encapsulating FK506. FASEB J. 27, 1362-1370 (2013). (Year: 2013).*
Maruyama et al. Targetability of novel immunoliposomes modified with amphipathic poly( ethylene glycol)s conjugated at their distal terminals to monoclonal antibodies. Biochimica et Biophysica Acta 1234 (1995) 74-80 (Year: 1995).*
Bahmani et al. Targeted delivery of immune therapeutics to lymp nodes prolongs cardiac allograft survival. J Clin Invest. 2018;128(11):4770-4786 (Year: 2018).*
Alam et al., "Enhanced trafficking to the pancreatic lymph nodes and auto-antigen presentation capacity distinguishes peritoneal B lymphocytes in non-obese diabetic mice," Diabetologia, Feb. 2010, 53: 346-355.
Azzi et al., "Polylactide-cyclosporin A nanoparticles for targeted immunosuppression," FASEB J., Oct. 2010, 24: 3927-3938.
Bergerot et al., "Insulin B-Chain Reactive CD4+ Regulatory T-Cells Induced by Oral Insulin Treatment Protect From Type 1 Diabetes by Blocking the Cytokine Secretion and Pancreatic Infiltration of Diabetogenic Effector T-Cells," Diabetes, Sep. 1999, 48: 1720-1729.

(Continued)

*Primary Examiner* — Maher M Haddad
(74) *Attorney, Agent, or Firm* — Fish & Richardson P.C.

(57) ABSTRACT

The present disclosure provides, inter alia, compositions comprising drug containing polymeric particles that mimic lymphocyte migration in vivo and can specifically deliver immunosuppressive or immunoregulatory drugs to lymphoid tissues and sites of chronic inflammation where T-cell activation and T-cell mediated injury are occurring. Methods of preparing and using these drug-containing polymeric particles are also provided.

7 Claims, 7 Drawing Sheets

(56) References Cited

OTHER PUBLICATIONS

Bird et al., "Single-chain antigen-binding proteins," Science, Oct. 1988, 242:423-426.
Bresson et al., "Anti-CD3 and nasal proinsulin combination therapy enhances remission from recent-onset autoimmune diabetes by inducing Tregs," J Clin Invest, May 2006, 116: 1371-1381.
Chamberlain et al., "Polymerization of Lactide with Zinc and Magnesium β-Diiminate Complexes: Stereocontrol and Mechanism," J. Am. Chem. Soc., Mar. 2001, 123(14): 3229-3238.
Cheng et al, "Magnetically Responsive Polymeric Microparticles for Oral Deliveryof Protein Drugs," Pharm Res., Mar. 2006, 23: 557-564.
Clare-Salzler and Mullen, "Marked dendritic cell-T cell cluster formation in the pancreatic lymph node of the non-obese diabetic mouse," Immunology, Jul. 1992, 76:478-484.
Dechy-Cabaret et al., "Controlled ring-opening polymerization of lactide and glycolide," Chemical Reviews, Dec. 2004, 104: 6147-6176.
Dong et al., "Vascular addressins in the uterus and pancreas of type 1 diabetic mice in early pregnancy," Placenta, Feb. 2008, 29: 201-209.
Fabien et al., "Pancreatic Lymph Nodes are Early Targets of T Cells during Adoptive Transfer of Diabetes in NOD Mice," J Autoimmun., Jun. 1995, 8: 323-334.
Faveeuw et al., "Expression of homing and adhesion molecules in infiltrated islets of Langerhans and salivary glands of nonobese diabetic mice," J Immunol, Jun. 1994, 152: 5969-5978.
Faveeuw et al., "Homing of lymphocytes into islets of Langerhans in prediabetic non-obese diabetic mice is not restricted to autoreactive T cells," Int Immunol, Dec. 1995, 7: 1905-1913.
Fiorina, "Immunomodulatory Function of Bone Marrow-Derived Mesenchymal Stem Cells in Experimental Autoimmune Type 1 Diabetes," J Immunol, Jul. 2009, 183: 993-1004.
Florescu et al., "Immune therapy for breast cancer in 2010—hype or hope?," Curr Oncol, Jan. 2011,18: e9-e18.
Gavalas et al., "Immune Response in Ovarian Cancer: How Is the Immune System Involved in Prognosis and Therapy: Potential for Treatment Utilization," Clinical & Developmental Immunology, 2010, 2010: 791603.
Halbreich et al., "Biomedical applications of maghemite ferrofluid," Biochimie, May-Jun. 1988, 80(5-6): 379-90.
Hanninen et al., "Mucosa-Associated (β7-integrin$^{high}$) Lymphocytes Accumulate Early in the Pancreas of NOD Mice and Show Aberrant Recirculation Behavior," Diabetes, Sep. 1996, 45: 1173-1180.
Hanninen et al., "Recirculation and homing of lymphocyte subsets: dual homing specificity of beta 7-integrin(high)-lymphocytes in nonobese diabetic mice," Blood, Aug. 1996, 88: 934-944.
Hemmerich., "Sulfation-dependent Recognition of High Endothelial Venules (HEV)-Ligands by L-Selectin and MECA 79, an Adhesion-blocking Monoclonal Antibody," J Exp Med, Dec. 1994, 180: 2219-2226.
Hirakawa et al., "Novel Anti-carbohydrate Antibodies Reveal the Cooperative Function of Sulfated N- and O-Glycans in Lymphocyte Homing," J Biol Chem, Dec. 2010, 285: 40864-40878.
Hogemann et al., "Improvement of MRI Probes to Allow Efficient Detection of Gene Expression," Bioconjug. Chem., Nov.-Dec. 2000, 11(6):941-946.
Hoglund et al., "Initiation of Autoimmune Diabetes by Developmentally Regulated Presentation of Islet Cell Antigens in the Pancreatic Lymph Nodes," J Exp Med, Jan. 1999, 189: 331-339.
Huston et al., "Protein engineering of antibody binding sites: recovery of specific activity in an anti-digoxin single-chain Fv analogue produced in *Escherichia coli*," PNAS, Aug. 1988, 85:5879-5883.
International Preliminary Report on Patentability in International Application No. PCT/US2015/010851, dated Jul. 19, 2016, 11 pages.

Josephson et al., "High-Efficiency Intracellular Magnetic Labeling with Novel Superparamagnetic-Tat Peptide Conjugates," Bioconjug. Chem., Mar.-Apr. 1999, 10(2):186-91.
Jurewicz et al., "Congenic Mesenchymal Stem Cell Therapy Reverses Hyperglycemia in Experimental Type 1 Diabetes," Diabetes, Dec. 2010, 59: 3139-3147.
Kai et al., "Prevention of insulitis and diabetes in nonobese diabetic mice by administration of FK506," Transplantation, Apr. 1993, 55: 936-940.
Katz et al., "Following a diabetogenic T cell from genesis through pathogenesis," Cell, Sep. 1993, 74: 1089-1100.
Kearney et al., "Visualization of peptide-specific T cell immunity and peripheral tolerance induction in vivo," Immunity, Jul. 1994, 1: 327-339.
Kurasawa et al., "The immunosuppressant FK-506 prevents progression of diabetes in nonobese diabetic mice," Clin Immunol Immunopathol, Nov. 1990, 57: 274-279.
Ley and Tedder, "Leukocyte interactions with vascular endothelium. New insights into selectin-mediated attachment and rolling," J Irnrnunol, Jul. 1995, 155: 525-528.
Ley et al., "Sequential contribution of L- and P-selectin to leukocyte rolling in vivo," J Exp Med, Feb. 1995, 181: 669-675.
Liu et al., "Expression of MAdCAM-1 and PNAd in Inflammatory and MALT Lymphoma Tissues of Ocular Adnexa, Thyroid, Salivary Gland and Lung," J Clin Exp Hematopathol, Apr. 2004, 44(1): 33-37.
Liu et al., "Calcineurin is a common target of cyclophilin-cyclosporin A and FKBP-FK506 complexes," Cell, Aug. 1991, 66 (4): 807-815.
Mackay, "Moving targets: cell migration inhibitors as new anti-inflammatory Therapies," Nat Immunol, Sep. 2008, 9: 988-998.
Matthews et al., "Developing combination immunotherapies for type 1 diabetes: recommendations from the ITN—JDRF Type 1 Diabetes Combination Therapy Assessment Group," Clin. Exp. Immunol., May 2010, 160: 176-184.
Michie et al., "The human peripheral lymph node vascular addressin. An inducible endothelial antigen involved in lymphocyte homing," Am J Pathol, Dec. 1993, 143:1688-1698.
Mikulowska-Mennis et al., "Lymphocyte Migration to Inflamed Lacrimal Glands Is Mediated by Vascular Cell Adhesion Molecule-1/α4β1 Integrin, Peripheral Node Addressin/L-Selectin, and Lymphocyte Function-Associated Antigen-1 Adhesion Pathways," Am J Pathol, Aug. 2001, 159: 671-681.
Nti et al., "Treg cells in pancreatic lymph nodes: the possible role in diabetogenesis and β cell regeneration in a T1D model," Cell Mol Immunol, Oct. 2012, 9: 455-463.
Peakman and von Herrath, "Antigen-Specific Immunotherapy for Type 1 Diabetes: Maximizing the Potential," Diabetes, Sep. 2010, 59: 2087-2093.
Penaranda and Bluestone, "Is Antigen Specificity of Autoreactive T Cells the Key to Islet Entry?," Immunity, Oct. 2009, 31: 534-536.
Polanski et al., "Oral administration of the immunodominant B-chain of insulin reduces diabetes in a co-transfer model of diabetes in the NOD mouse and is associated with a switch from Th1 to Th2 cytokines," J Autoimmun , Aug. 1997, 10: 339-346.
Roncarolo and Battaglia, "Regulatory T-cell immunotherapy for tolerance to self antigens and alloantigens in humans," Nat Rev Immunol., Aug. 2007, 7: 585-598.
Rosen et al., "Therapeutic Targeting of Endothelial Ligands for L-selectin (PNAd) in a Sheep Model of Asthma," Am J Pathol, Mar. 2005, 166: 935-944.
Shapiro et al., "Combination therapy with low dose sirolimus and tacrolimus is synergistic in preventing spontaneous and recurrent autoimmune diabetes in non-obese diabetic mice," Diabetologia, Feb. 2002, 45: 224-230.
Sherry et al., "Exendin-4 Improves Reversal of Diabetes in NOD Mice Treated with Anti-CD3 Monoclonal Antibody by Enhancing Recovery of β-Cells," Endocrinology, 2007, 148: 5136-5144.
Somers et al., "Insights into the Molecular Basis of Leukocyte Tethering and Rolling Revealed by Structures of P- and E-Selectin Bound to SLeX and PSGL-1," Cell, Oct. 2000, 103: 467-479.

(56) References Cited

OTHER PUBLICATIONS

Streeter et al., "Immunohistologic and Functional Characterization of a Vascular Addressin Involved in Lymphocyte Homing into Peripheral Lymph Nodes," J. Cell. Biol., Nov. 1988, 107:1853-1862.
Takiishi et al., "Reversal of autoimmune diabetes by restoration of antigen-specific tolerance using genetically modified Lactococcus lactis in mice," J Clin Invest, May 2012, 122: 1717-1725.
Tang et al., "Immunosuppressive Activity of Size-Controlled PEG-PLGA Nanoparticles Containing Encapsulated Cyclosporine A," J. Transplantation, Mar. 2012, 2012: 896141.
Tedder et al., "The selectins: vascular adhesion molecules," FASEB J, Jul. 1995, 9: 866-873.
Teply et al., "The Use of Charge-Coupled Polymeric Microparticles and Micromagnets for Modulating the Bioavailability of Orally Delivered Macromolecules," Biomaterials, Mar. 2008, 29: 1216-1223.
Tiwari, "From tumor immunology to cancer immunotherapy: miles to go," J Cancer Res Ther, Oct.-Dec. 2010, 6: 427-431.
Tong and Cheng, "Anticancer Polymeric Nanomedicines," J. Polymer Reviews, Aug. 2007, 47: 345-381.
Tong and Cheng, "Drug-Initiated, Controlled Ring-Opening Polymerization for the Synthesis of Polymer-Drug Conjugates," Macromolecules, 45: 2225-2232.
Tong and Cheng, "Paclitaxel-Initiated, Controlled Polymerization of Lactide for the Formulation of Polymeric Nanoparticulate Delivery Vehicles," J. Angew. Chem. Int. Ed., Jun. 2008, 47: 4908-4912.
Tong and Cheng, "Ring-Opening Polymerization-Mediated Controlled Formulation of Polylactide Drug Nanoparticles," J. Am. Chem. Soc., Mar. 2009, 131: 4744-4754.
Tong et al., "The formulation of aptamer-coated paclitaxel-polylactide nanoconjugates and their targeting to cancer cells," Biomaterials, Feb. 2010, 31: 3043-3053.
Turley et al., "Endocrine self and gut non-self intersect in the pancreatic lymph nodes," PNAS, Dec. 2005, 102: 17729-17733.
Turley et al., "Physiological β Cell Death Triggers Priming of Self-reactive T Cells by Dendritic Cells in a Type-1 Diabetes Model," J. Exp Med, Nov. 2003, 198: 1527-1537.
Valle et al., "Rapamycin Prevents and Breaks the Anti-CD3-Induced Tolerance in NOD Mice," Diabetes, Apr. 2009, 58: 875-881.
Von Andrian and Mackay, "T-cell function and migration. Two sides of the same coin," N Engl J Med, Oct. 2000, 343: 1020-1034.
Von Herrath et al., "Oral insulin treatment suppresses virus-induced antigen-specific destruction of beta cells and prevents autoimmune diabetes in transgenic mice," J Clin Invest, Sep. 1996, 98: 1324-1331.
Xu et al., "Lymphocyte Homing to Bronchus-associated Lymphoid Tissue (BALT) Is Mediated by L-selectin/PNAd, α4β1 Integrin/VCAM-1, and LFA-1 Adhesion Pathways," J Exp Med, May 2003, 197: 1255-1267.
Xu et al., "α4β7 integrin/MAdCAM-1 adhesion pathway is crucial for B cell migration into pancreatic lymph nodes in nonobese diabetic mice," J Autoimmun., Sep. 2010, 35: 124-129.
Yang et al., "A predominant role of integrin a!4 in the spontaneous development of autoimmune diabetes in nonobese diabetic mice," PNAS, Dec. 1994, 91: 12604-12608.
Yang et al., "Cell Adhesion Molecules: A Selective Therapeutic Target for Alleviation of IDDM," J Autoimmun, Dec. 1994, 7: 859-864.
Yuan et al., "The Role of the CD134-CD134 Ligand Costimulatory Pathway in Alloimmune Responses In Vivo," J Immunol, Mar. 2003,170: 2949-2955.
Zhang et al., "Suppression of diabetes in nonobese diabetic mice by oral administration of porcine insulin," PNAS, Nov. 1991, 88: 10252-10256.
International Search Report and Written Opinion dated Apr. 13, 2015 in international application No. PCT/US2015/010851, 19 pgs.
Hauff, P et al., "Molecular Targeting of Lymph Nodes With L-Selectin Ligand-Specific US Contrast Agent: A Feasibility Study in Mice and Dogs." Radiology. Apr. 29, 2004, vol. 231, No. 3; pp. 667-673.
Berg, EL et al., "The Human Peripheral Lymph Node Vascular Addressin Is a Ligand for LECAM-1, the Peripheral Lymph Node Homing Receptor." The Journal of Cell Biology. 1991, vol. 114, No. 2; pp. 343-349.
Muzykantov, VR, "Targeted Drug Delivery to Endothelial Adhesion Molecules." ISRN Vascular Medicine. Jun. 9, 2013, vol. 2013, article ID. 916254.
Shaji, J et al., "Nanocarriers for Targeting in Inflammation. Asian Journal of Pharmaceutical and Clinical Research." Sep. 2013, vol. 6, No. 3; pp. 3-12.
Michie, SA et al., "L-Selectin and alpha4beta7 Integrin Homing Receptor Pathways Mediate Peripheral Lymphocyte Traffic to AKR Mouse Hyperplastic Thymus." American Journal of Pathology. Aug. 1995, vol. 147, No. 2; pp. 412-421.
Pals, ST et al., "Lymphoma Dissemination: The Other Face of Lymphocyte Homing." Blood. Jul. 26, 2007, vol. 110, No. 9; pp. 3102-3111.

* cited by examiner

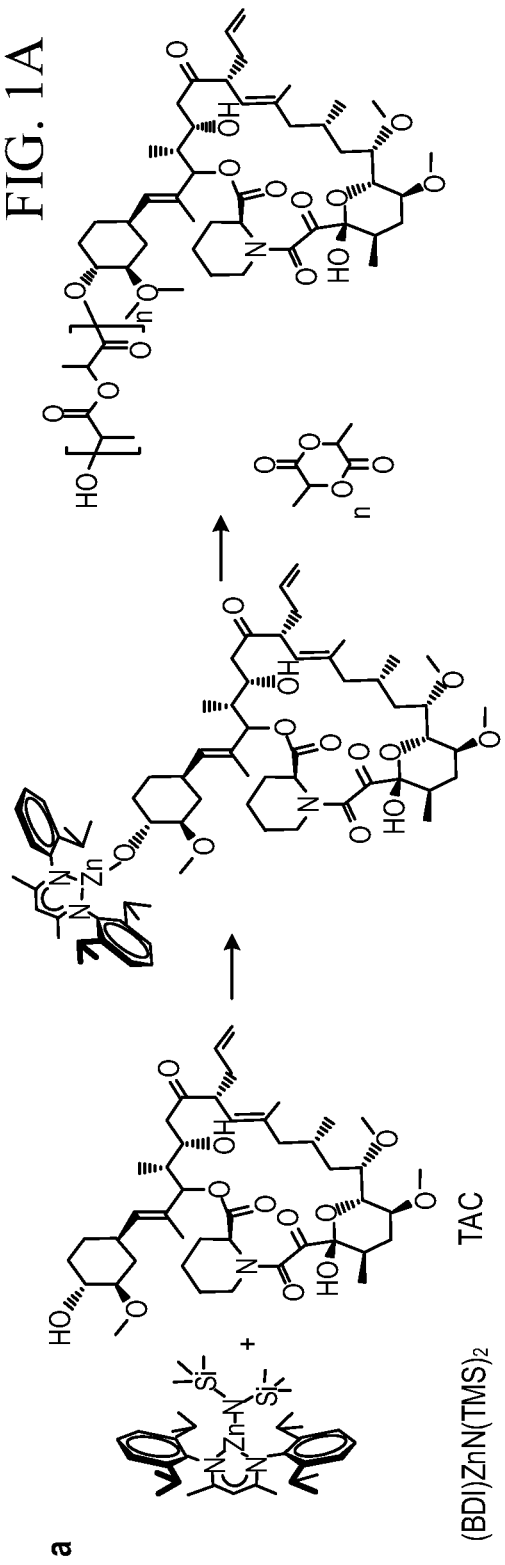
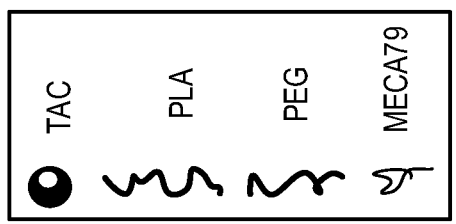
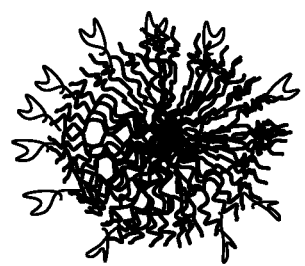
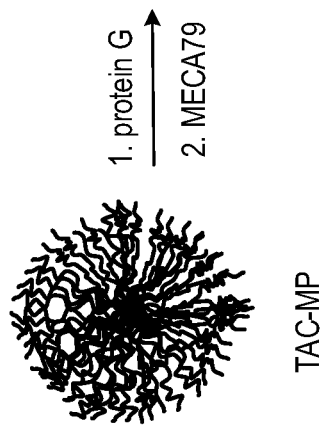
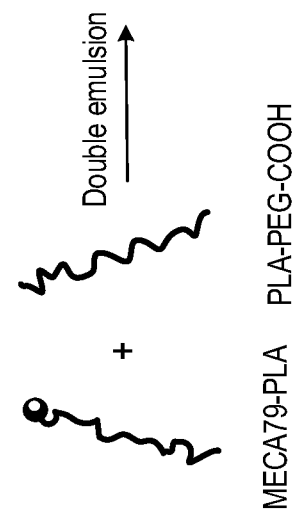
FIG. 1A
FIG. 1B

FIG. 2A
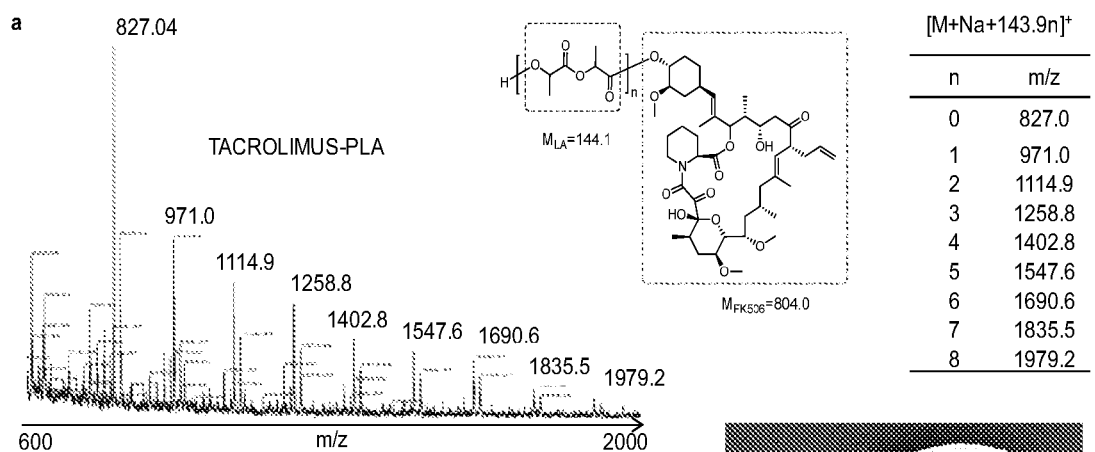
| n | m/z |
|---|---|
| 0 | 827.0 |
| 1 | 971.0 |
| 2 | 1114.9 |
| 3 | 1258.8 |
| 4 | 1402.8 |
| 5 | 1547.6 |
| 6 | 1690.6 |
| 7 | 1835.5 |
| 8 | 1979.2 |
$[M+Na+143.9n]^+$
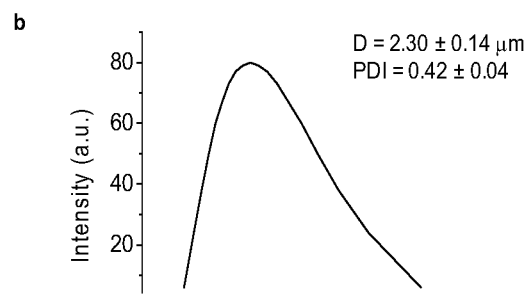
FIG. 2B
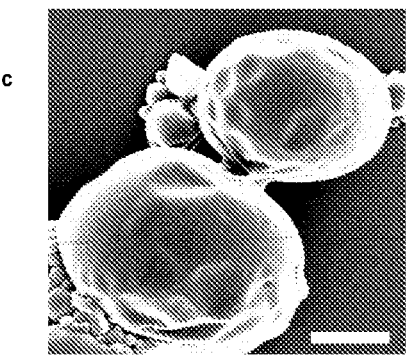
FIG. 2C

FIG. 7
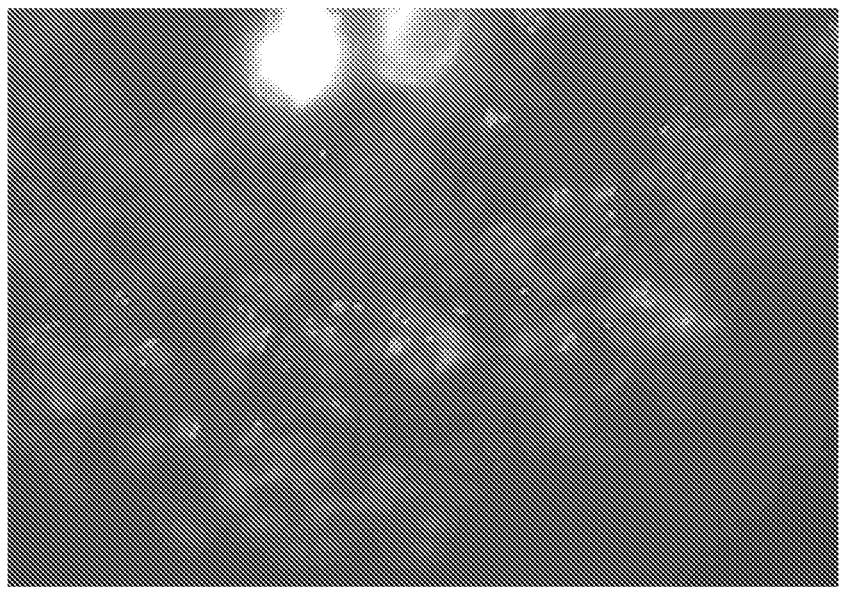
FIG. 8A   FIG. 8B   FIG. 8C
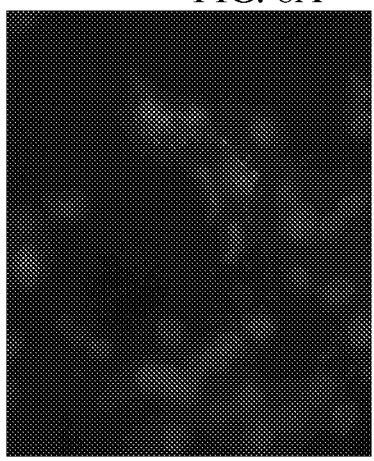 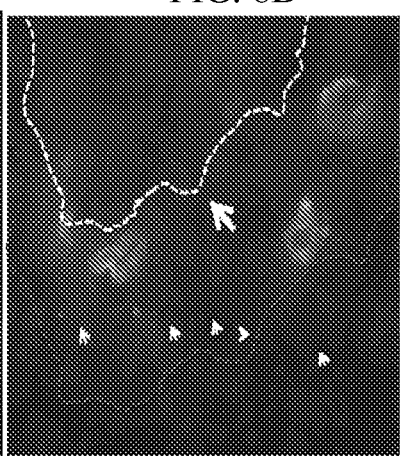 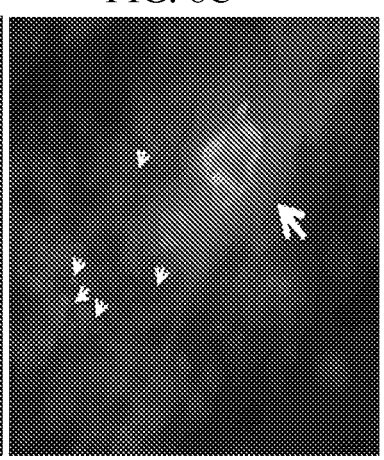

FIG. 9A
FIG. 9B
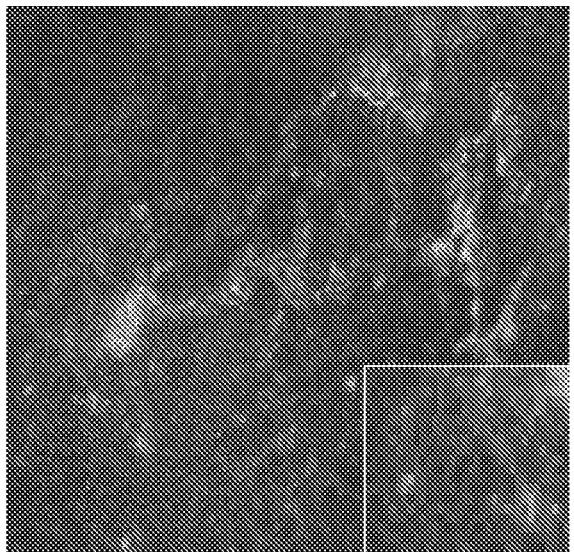
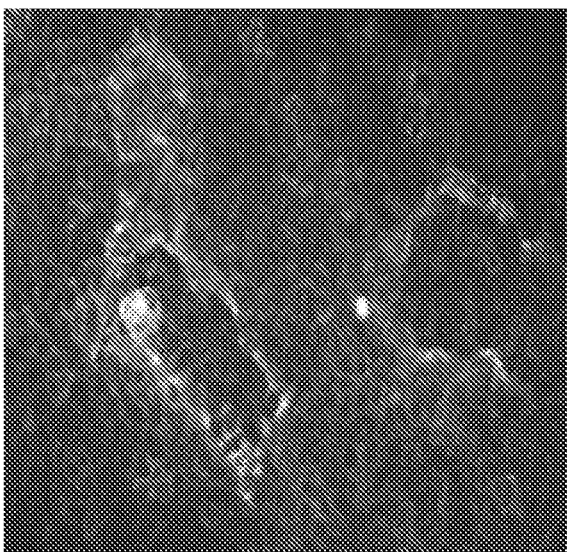
FIG. 10A
FIG. 10B
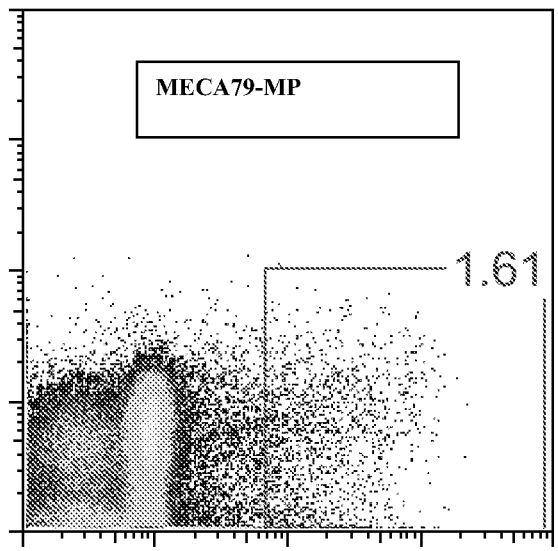
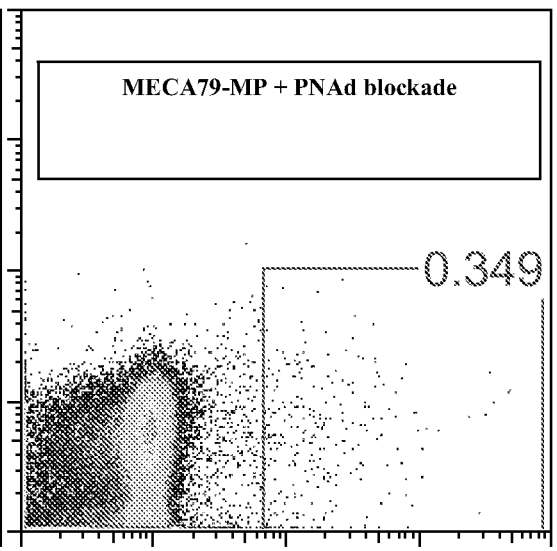

TARGETED DELIVERY OF IMMUNOREGULATORY DRUGS

CLAIM OF PRIORITY

This application is a § 371 National Stage Application of PCT/US2015/010851, filed Jan. 9, 2015, which claims priority to U.S. Provisional Patent Application Ser. No. 61/928,231, filed on Jan. 16, 2014. The entire contents of the foregoing are hereby incorporated by reference.

FEDERALLY SPONSORED RESEARCH OR DEVELOPMENT

This invention was supported by Government support under Grant No. RO1 5R01AI091930 awarded by the National Institute of Allergy and Infectious Diseases (NIAID) of the National Institutes of Health. The Government has certain rights in the invention.

TECHNICAL FIELD

This invention relates to methods and compositions for targeted delivery of immunoregulatory drugs to lymphoid tissues and sites of chronic inflammation.

BACKGROUND

Inflammation is a key pathogenic process in a very large number of prevalent diseases from classical immune-mediated diseases such as rheumatoid arthritis to cancer. From graft rejection where leukocytes invade the transplanted organ, to multiple sclerosis where lymphocytes invade brain to atherosclerotic plaque where leukocytes aggravate lipid induced micro and macro-vascular injuries, immune or inflammatory responses are central to the development of these diseases. The past decade has witnessed major advancements in the development of new immunosuppressive drugs. These drugs have played a pivotal role in ensuring the success of organ transplantation and have greatly improved the outcomes of patients with life-threatening, immune-mediated diseases. However, the use of immunosuppressive agents is hindered by the lack of selectivity and frequently observed major adverse drug reactions.

SUMMARY

The present disclosure is based, at least in part, on the development of drug-containing polymeric particles that mimic lymphocyte migration in vivo and can specifically deliver immunosuppressive or immunoregulatory drugs to lymphoid tissues and sites of chronic inflammation where T-cell activation and T-cell mediated injury are occurring. Specifically, the drug-containing polymeric particles described herein are attached (chemically linked) to a molecule that regulates lymphocyte homing, e.g., a lymphocyte homing adhesion molecule, e.g., L-selectin, or an antibody that binds a ligand of the lymphocyte homing adhesion molecule, e.g., an antibody that binds peripheral lymph node addressin (PNAd) expressed on high endothelial venules, e.g., MECA-79 or newer antibodies such as S1 and S2.

In one aspect, the present disclosure provides compositions that include one or more drug-containing polymeric particles, each attached to a lymphocyte homing adhesion molecule or an antibody that binds a ligand of the lymphocyte homing adhesion molecule. The one or more drug-containing polymeric particles comprise an immunosuppressive or immunoregulatory drug. In some embodiments, the one or more drug-containing polymeric particles comprise a polymer selected from polylactide, polyglycolide, or poly (lactic-co-glycolic) acid.

In some embodiments, the one or more drug-containing polymeric particles are each attached to a lymphocyte homing adhesion molecule. The lymphocyte homing adhesion molecule can be selected from L-selectin, cutaneous lymphocyte antigen (CLA), α4β7 integrin, αEβ7 integrin, αLβ2 integrin, and α4β1 integrin.

In some embodiments, the one or more drug-containing polymeric particles are each attached to L-selectin.

In some embodiments, the one or more drug-containing polymeric particles are each attached to an antibody that binds a ligand of the lymphocyte homing adhesion molecule. The ligand of the lymphocyte homing adhesion molecule can be selected from peripheral lymph node addressin (PNAd), E-selectin, mucosal addressin cell adhesion molecule (MAdCAM-1), E-cadherin, intercellular adhesion molecule 1 (ICAM-1), intercellular adhesion molecule 2 (ICAM-2), vascular cell adhesion molecule 1 (VCAM-1).

In some embodiments, the one or more drug-containing polymeric particles are each attached to an antibody that binds PNAd, e.g., MECA-79 or S2 monoclonal antibody.

In some embodiments, e.g., to target the drug-containing polymeric particles disclosed herein to peripheral lymph nodes, the particles can be coated with L-selectin or an antibody that binds PNAd, e.g., MECA-79 or S2 monoclonal antibodies.

In some embodiments, e.g., to target drug-containing polymeric particles disclosed herein to skin, the particles can be coated with cutaneous lymphocyte antigen (CLA), or antibody that binds E-selectin.

In some embodiments, e.g., to target the drug-containing polymeric particles to gastrointestinal tract, the particles disclosed herein can be coated with α4β7 integrin or an antibody that binds MAdCAM-1.

In some embodiments, e.g., to target the drug-containing polymeric particles to epithelium, the particles disclosed herein can be coated with αEβ7 integrin or an antibody that binds E-cadherin.

In some embodiments, e.g., to target the drug-containing polymeric particles to bone marrow and inflammatory sites, the particles disclosed herein can be coated with α4β1 integrin or an antibody that binds VCAM-1.

In some embodiments, e.g., to target the drug-containing polymeric particles to multiple lymphoid tissues, the particles disclosed herein can be coated with αLβ2 integrin or an antibody that binds ICAM-1 or ICAM-2.

In some embodiments, the one or more drug-containing polymeric particles are covalently conjugated to the lymphocyte homing adhesion molecule or an antibody that binds a ligand of the lymphocyte homing adhesion molecule.

In some embodiments, the one or more drug-containing polymeric particles are attached to the lymphocyte homing adhesion molecule or an antibody that binds a ligand of the lymphocyte homing adhesion molecule through a linker, e.g., polyethylene glycol.

In some embodiments, the drug-containing polymeric particles are prepared by polymerizing one or more cyclic monomers in the presence of a drug comprising one or more hydroxyl or thiol groups and a ring-opening polymerization catalyst, with the drug serving as the initiator of the polymerization reaction. The one or more cyclic monomers can be selected from the group consisting of cyclic esters, cyclic carbonates, cyclic phosphates, cyclic siloxanes, cyclic peptides or amino acid derivative, and cyclic phosphazenes. For example, the cyclic monomer can be lactide or glycolide. In some embodiments, the drug comprising one or more hydroxyl or thiol groups is an immunosuppressive or immunoregulatory drug. In some embodiments, the ring-opening polymerization catalyst is selected from a Zn, Mg, Ca, and Fe catalyst. In some embodiments, the ring-opening polymerization catalyst is a Zn catalyst, e.g., $(BDI)ZnN(TMS)_2$.

In some embodiments, the compositions disclosed herein also include a pharmaceutically acceptable carrier.

In another aspect, the present disclosure provides methods of suppressing a lymphocyte-mediated immune response in a subject. The methods include identifying a subject in need of suppressing a lymphocyte-mediated immune response; and administering to the subject a therapeutically effective amount of the composition disclosed herein.

In another aspect, the present disclosure provides methods of preventing, treating or delaying progression of autoimmune diseases, e.g., autoimmune diabetes, e.g., type 1 diabetes, in a subject. The methods include identifying a subject in need of treatment for autoimmune diseases, e.g., autoimmune diabetes, and administering to the subject a therapeutically effective amount of the composition disclosed herein.

In another aspect, the present disclosure provides methods of treating lymphocyte-mediated inflammation in a subject. The methods include identifying a subject in need of treatment for lymphocyte-mediated inflammation; and administering to the subject a therapeutically effective amount of the composition disclosed herein.

In yet another aspect, the present disclosure provides methods of treating or reducing the metastasis of a PNAd-expressing malignancy, e.g., PNAd-expressing lymphomas, in a subject. The methods include identifying a subject in need of treatment for PNAd-expressing malignancy, and administering to the subject a therapeutically effective amount of the drug-containing polymeric particles coated with L-selectin or an antibody that binds PNAd described herein.

In another aspect, the present disclosure provides methods of delivering a drug to a subject by administering a therapeutically effective amount of the composition disclosed herein to the subject.

In another aspect, the present disclosure provides methods of delivering an immunosuppressive or immunoregulatory drug to lymphoid tissues or sites of chronic inflammation in a subject. These methods include (1) providing one or more drug-containing polymeric particles comprising the immunosuppressive or immunoregulatory drug coated with L-selectin or an antibody that binds PNAd; and (2) administering the one or more drug-containing polymeric particles to the subject.

As used herein, the term "polymer" means a chemical species containing a plurality of repeating units that are bonded to each other. A polymer may contain more than one different repeating unit. The repeating unit typically derives from polymerization of a monomer. A copolymer specifically refers to a polymer containing two or more structurally different repeating units. The different repeating units of a polymer may be randomly ordered in the polymer chain or the same repeating units may be grouped into contiguous blocks in the polymer. When there are contiguous blocks of the two or more repeating units in a polymer, the polymer is a block copolymer.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient of the symptoms, that can be attributed to or associated with treatment by the compositions and methods of the present disclosure.

The terms "effective amount" and "effective to treat," as used herein, refer to an amount or a concentration of one or more of the compositions described herein utilized for a period of time (including acute or chronic administration and periodic or continuous administration) that is effective within the context of its administration for causing an intended effect or physiological outcome.

The term "subject" is used throughout the specification to describe an animal, human or non-human, rodent or non-rodent, to whom treatment according to the methods of the present disclosure is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a graph illustrating the synthesis of TAC-PLA particles by means of TACROLIMUS (TAC)-initiated lactide polymerization in the presence of (BDI)ZnN(TMS)2. FIG. 1B is the schematic illustration of preparation of poly(ethyleneglycol)ated (PEGylated) TAC-PLA particles with surface modified by MECA79 antibody.

FIG. 2A shows MALDI-TOF analysis for TAC-PLA conjugates. FIG. 2B shows dynamic light scattering (DLS) measurement of TAC-containing microparticles coated with MECA79. (D=average diameter; PDI=polydispersity index). FIG. 2C is a representative scanning electron microscope (SEM) image of TAC-containing microparticles coated with MECA79 antibody (TAC-MP-MECA79).

FIG. 7 is an immunohistochemistry image showing the presence of rhodamine-labeled MECA79-coated particles in pancreatic lymph nodes (PLN) of three-week old NOD mice. Medium grey areas (blue in original images) represented DAPI staining; lighter grey (red in original images) represented the rhodamine-labeled particles.

FIGS. 8A-8C are immunohistochemistry images showing the presence of rhodamine-labeled MECA79-coated particles in the pancreas of a NOD mouse. FIG. 8A is an immunohistochemistry image of the pancreas of a NOD mouse showing the presence of rhodamine-labeled MECA79-coated particles (red) in the pancreas. Medium grey areas (blue in original images) represented DAPI staining; lighter grey (red in original images) represented the rhodamine-labeled particles. FIGS. 8B and 8C are immunohistochemistry images showing accumulation of rhodamine-labeled MECA79-coated particles (red in original images, small arrows in 8C) around PNAd-expressing peri-islet vasculatures (white, large arrows in 8C) that surround the insulin-expressing islets (white line in 8B) outlined by dense lymphocytes (grey line in 8B). Green color in the original represented insulin staining (lighter grey areas due to insulitis inside the white line in 8B); white color represented PNAd staining; medium grey (blue in original) represented DAPI staining and the islet was outlined by dense DAPI-positive lymphocytes (grey line in 8B); dark grey dots (red in original) represented the rhodamine-labeled particles.

FIGS. 9A and 9B are immunohistochemistry images of inguinal lymph nodes showing higher trafficking of MECA79-coated particles to the draining lymph nodes following intravenous administration. Higher number of MECA79-coated particles (lighter dots; red in the original) were trafficked to the draining lymph nodes (9A) as compared to particles without MECA79 (9B). Diffuse dark grey blue in the original represents DAPI staining; medium grey (green in original) represents PNAd staining; lighter grey (red in original, in 9A only) represents the rhodamine-labeled particles (magnification×200).

FIGS. 10A and 10B are FACS plots showing that preferential trafficking of MECA79-coated particles to the draining LNs is reduced by blocking PNAd in vivo.

DETAILED DESCRIPTION

Figure 3:
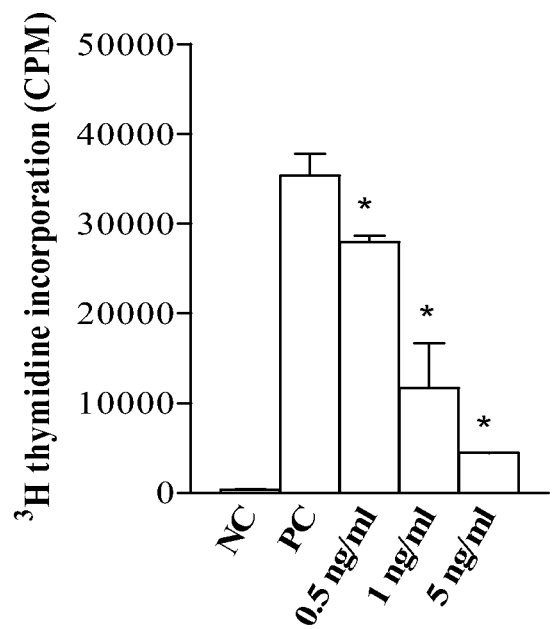
FIG. 3 is a bar graph showing dose-dependent suppression of T cell proliferation by TAC-MP-MECA79 (* $P<0.05$).

The present disclosure is based, at least in part, on the development of drug-containing polymeric particles that mimic lymphocyte migration in vivo and can specifically deliver immunosuppressive or immunoregulatory drugs to lymphoid tissues and sites of chronic inflammation where T-cell activation and T-cell mediated injury are occurring. Specifically, the drug-containing polymeric particles described herein are attached (linked) to a molecule that regulates lymphocyte homing, e.g., a lymphocyte homing adhesion molecule, e.g., L-selectin, or an antibody that binds a ligand of the lymphocyte homing adhesion molecule, e.g., an antibody that binds PNAd expressed on high endothelial venules, e.g., MECA-79 or S2 monoclonal antibody.

Activation of immune cells against either autoantigens in autoimmune diseases or exogenous antigens occurs in lymphoid tissues, from which the activated immune cells travel to lymphoid tissues and peripheral organs and cause damages there. Delivery of a small amount of immunosuppressive or immunoregulatory drugs directly to the sites where the damages are occurring can increase efficacy of the treatment and minimize toxicity seen in systemic administration of a large amount of immunosuppressive medications.

The present disclosure provides, inter alia, compositions and methods useful for delivering immunosuppressive or immunoregulatory drugs directly to the diseased lymphoid tissues and sites of chronic inflammation.

The compositions disclosed herein include one or more drug-containing polymeric particles, each of which are attached to a molecule that regulates lymphocyte homing, e.g., a lymphocyte homing adhesion molecule, or an antibody that binds a ligand of the lymphocyte homing adhesion molecule. The lymphocyte homing adhesion molecules include L-selectin, cutaneous lymphocyte antigen (CLA), α4β7 integrin, αEβ7 integrin, αLβ2 integrin, and α4β1 integrin. The ligands for the lymphocyte homing adhesion molecules include peripheral lymph node addressin (PNAd), E-selectin, mucosal addressin cell adhesion molecule (MAd-CAM-1), E-cadherin, intercellular adhesion molecule 1 (ICAM-1), intercellular adhesion molecule 2 (ICAM-2), vascular cell adhesion molecule 1 (VCAM-1). Exemplary antibodies against PNAd, a ligand of the lymphocyte homing adhesion molecule L-selectin, include MECA-79 and S2 monoclonal antibodies.

Drug-Containing Polymeric Particles

The nano- or microparticles described herein can be made of materials that (i) are biocompatible, i.e., do not cause a significant adverse reaction in a living animal when used in pharmaceutically relevant amounts; (ii) feature functional groups to which a lymphocyte homing adhesion molecule or an antibody that binds a ligand of the lymphocyte homing adhesion molecule can be covalently attached, (iii) exhibit low non-specific binding to other molecules, and (iv) are stable in solution, i.e., the particles do not precipitate. The particles can be monodisperse (a single crystal of a material, e.g., a metal, per particle) or polydisperse (a plurality of crystals, e.g., 2, 3, or 4, per particle).

A number of biocompatible particles are known in the art, e.g., organic or inorganic nano- or microparticles. Liposomes, dendrimers, carbon materials and polymeric micelles are examples of organic particles. Quantum dots can also be used. Inorganic particles include metallic particle, e.g., Au, Ni, Pt and TiO2 nano- or microparticles. Magnetic particles can also be used, e.g., spherical nanocrystals of 10-20 nm with a $Fe^{2+}$ and/or $Fe^{3+}$ core surrounded by dextran or PEG molecules. Colloidal gold nanoparticles are described in e.g., Qian et. al., Nat. Biotechnol. 26(1):83-90 (2008); U.S. Pat. Nos. 7,060,121; 7,232,474; and U.S. P.G. Pub. No. 2008/0166706. Suitable nanoparticles, and methods for constructing and using multifunctional nanoparticles, are discussed in e.g., Sanvicens and Marco, Trends Biotech., 26(8): 425-433 (2008).

In all embodiments, the nano- or microparticles are attached (linked) to a lymphocyte homing adhesion molecule or an antibody that binds a ligand of the lymphocyte homing adhesion molecule described herein via a functional groups. In some embodiments, the nano- or microparticles are associated with a polymer that includes the functional groups, and also serves to keep the metal oxides dispersed from each other. The polymer can be a synthetic polymer, such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxmethyl dextran, and/or reduced carboxymethyl dextran. The metal oxide can be a collection of one or more crystals that contact each other, or that are individually entrapped or surrounded by the polymer.

In other embodiments, the nano- or microparticles are associated with non-polymeric functional group compositions. Methods are known to synthesize stabilized, functionalized nano- or microparticles without associated polymers, which are also within the scope of this invention. Such methods are described, for example, in Halbreich et al., Biochimie, 80 (5-6):379-90, 1998.

In some embodiments, an immunosuppressive or immunoregulatory drug described herein can be encapsulated within, e.g., mixed within or under a coating of, the nano- or microparticles. In some embodiments, an immunosuppressive or immunoregulatory drug described herein can be conjugated with, e.g., outside the surface of, the nano- or microparticles.

Immunosuppressive or Immunoregulatory Drugs

Three classical immunosuppressive drugs, Cyclosporine A, Rapamycin, and Tacrolimus have been successfully incorporated into the drug-containing particles described herein, which showed controlled drug release and suppression of T cell activity in vitro (Azzi, J., et al., FASEB J 24: 3927-3938, 2010; Tang, L., et al., J. Transplantation, 2012: 896141, 2012; Tong, R. & Cheng, J. J., Macromolecules 45: 2225-2232, 2012).

In some embodiments, Tacrolimus (also known as TAC, FK-509, or fujimycin) is incorporated into the drug-containing particles described herein. Tacrolimus is an immunosuppressive drug that is mainly used after allogeneic organ transplant to reduce the host's immune responses and lower the risk of organ rejection. At the molecular level, Tacrolimus is a macrolide lactone that can reduce interleukin-2 (IL-2) production by the T-cells (Liu J, Farmer J, Lane W, Friedman J, Weissman I, Schreiber S, Cell 66 (4): 807-815, 1991). Other suitable immunosuppressive or immunoregulatory drugs that can be incorporated into the present delivery system include, but are not limited to, mycophenolate, mofetil, cyclosporine, sirolimus, fingolimod, myriocin, and monoclonal antibodies such as anti-CD3 antibody, anti-CD25 antibody, anti-IL6 antibody, CTLA-4-Ig, and adalimumab. In some embodiments, the immunosuppressive or immunoregulatory drugs have one or more hydroxyl groups or thiol groups and can function as polymerization initiators in the presence of certain catalysts.

Synthesis of Drug-Containing Polymeric Particles

There are a variety of ways that the drug-containing nano- or microparticles can be prepared, but in all methods, the result must be a particle with functional groups that can be used to link the particle to a lymphocyte homing adhesion molecule or an antibody that binds a ligand of the lymphocyte homing adhesion molecule described herein.

In some embodiments, an immunosuppressive or immunoregulatory drug described herein can be encapsulated within, e.g., mixed within or under a coating of, the nano- or microparticles. Such drug-encapsulated particles can be synthesized using a nanoprecipitation method, e.g., described in Tang, L., et al., J. Transplantation, 2012: 896141, 2012, the content of which is incorporated by reference herein. Briefly, a drug to be delivered and PEGylated polymers can be dissolved in a suitable organic solvent. The resulting solution can be added dropwise into a nonsolvent, e.g., water, under vigorous stirring to form PEGylated drug-encapsulated polymeric particles. The particle suspension can then be stirred at room temperature to evaporate the organic solvent. An aliquot of the particle suspension can be centrifuged and the supernatant can be analyzed, e.g., by a reverse phase HPLC, to determine the incorporation efficiency and loading of the drug into the particles. The particles can then be purified and collected, e.g., by ultrafiltration. Optionally, a lyoprotectant, e.g., bovine serum albumin (BSA), can be added to the particle solution, which can then be lyophilized and stored at −20° C. The size and polydispersity of the resulting particles can be determined by dynamic light scattering (DLS) and/or scanning electron microscope (SEM).

In some embodiments, an immunosuppressive or immunoregulatory drug described herein can be conjugated with, e.g., outside the surface of, the nano- or microparticles. Such drug-conjugated particles can be synthesized using methods described in e.g., Azzi, J., et al., FASEB J 24: 3927-3938, 2010, or in the international application publication WO 2008/109483, the contents of which are incorporated by reference herein. Briefly, a drug to be delivered can be mixed with one or more cyclic monomers and a catalyst in a suitable solvent. The drug serves as an initiator in a ring-opening polymerization reaction to form drug-polymer conjugates in which the drug is covalently bonded to the polymer. Because the drug is used as the initiator of polymerization, the efficiency of conjugation of the drug to the polymer is very high, and the drug-loading percentage can be controlled by adjusting the monomer/initiator ratio. The drug-polymer conjugates and PEGylated polymers can then be added dropwise into a nonsolvent, e.g., water, under vigorous stirring to form PEGylated drug-conjugated polymeric particles. The particle suspension can then be stirred at room temperature to evaporate the organic solvent. The particles can be purified and collected, e.g., by ultrafiltration. Optionally, a lyoprotectant, e.g., bovine serum albumin (BSA), can be added to the particle solution, which can then be lyophilized and stored at −20° C. The size and polydispersity of the resulting particles can be determined by dynamic light scattering (DLS) and/or scanning electron microscope (SEM).

Suitable monomers for the ring-opening polymerization include various cyclic monomers, e.g., cyclic esters, cyclic carbonates, cyclic siloxanes, cyclic phosphates, cyclic peptides or amino acid derivative, or cyclic phosphazenes. Exemplified cyclic monomers include lactide or glycolide.

The polymeric particles described herein can be used to deliver any small molecule drug that contains at least one functional group capable of initiating the ring-opening polymerization reaction, e.g. a hydroxyl group or a thiol group. The drug may contain a plurality of such polymerization initiation groups, e.g., a plurality of hydroxyl groups or thiol groups. In some embodiments, the drug contains only one of such polymerization groups. The hydroxyl groups may be primary, secondary or tertiary hydroxyl groups. Similarly, the thiol groups may be primary, secondary or tertiary thiol groups. The hydroxyl group may also be a phenolic hydroxyl group. In some embodiments, the drug contains one or more non-phenolic hydroxyl groups. In some embodiments, the drug contains one or more non-phenolic hydroxyl groups that are primary or secondary hydroxyl groups. In some embodiments, the drug contains a single nonphenolic hydroxyl group. In some embodiments, the drug contains a single primary or secondary hydroxyl group. In some embodiments, the immunosuppressive or immunoregulatory drugs having one or more hydroxyl groups or thiol groups function as polymerization initiators in the presence of certain catalysts.

A number of catalysts can be employed to facilitate formation of the drug-containing polymeric particles. Exemplary catalysts include numerous metal-oxides (M-ORs) and alcohol-metal oxides (RO-M) developed for controlled, living polymerization of cyclic monomers (O. Dechy-Cabaret, B. Martin-Vaca, & D. Bourissou, Chemical Reviews 104: 6147-6176, 2004). Metal-oxides can be prepared in situ by mixing a hydroxyl-containing compound with an active metal-amido complex, such as a metal-amido compound (B. M. Chamberlain, M. Cheng, D. R. Moore, T. M. Ovitt, E. B. Lobkovsky, G. W. Coates, J. Am. Chem. Soc. 123: 3229, 2001). For example, $(BDI)MgN(TMS)_2$, a very active catalyst for the polymerization of lactide, can be employed (Chamberlain, 2001). Certain Zn catalysts, e.g., $(BDI)ZnN(TMS)_2$, facilitate fast initiation and relatively slow chain propagation, and can be used as catalyst for the polymerization. Zn-mediated lactide polymerization can result in polymers with narrow polydispersity. Other useful catalysts include Ca and Fe catalysts. Since Mg, Zn, Ca, and Fe are elements found in human body, catalysts containing these elements have a better safety profile than other active catalysts containing Al and Sn. Exemplary Zn, Mg, Ca and Fe catalysts, include the organocatalysts are described in WO 2008/109483. In some embodiments, a Zn catalyst, e.g., (BDI)ZnN(TMS)2, is used to initiate the drug-containing polymeric particles.

The particles described herein have shown high drug loading (about 50%) and loading efficiency (98-100%), well-controlled drug release kinetics without a burst release effect and excellent controlled particle size with a very narrow size distribution (Tong, R. & Cheng, J., Angew. Chem., Int. Ed. 47: 4830-4834, 2008; Tong, R. & Cheng, J., J. Am. Chem. Soc. 131: 4744-4754, 2009).

Particle size can be controlled by adjusting reaction conditions, for example, by varying temperature as described in U.S. Pat. No. 5,262,176. Uniform particle size materials can also be made by fractionating the particles using centrifugation, ultrafiltration, or gel filtration, as described, for example in U.S. Pat. No. 5,492,814.

The size of the drug-containing polymeric particles described herein can range from about 2 nm to about 500 µm. In some embodiments, the drug-containing polymer particles have an overall size ranging from about 0.01 µm to about 10 µm, e.g., about 0.05 µm to about 5 µm, about 0.1 µm to about 3 µm, about 1 µm to about 2.5 µm. In some embodiments, the drug-containing polymeric particles have an overall size ranging from about 500 nm to about 5 µm. In some embodiments, the drug-containing polymeric particles have an overall size ranging from about 1 µm to about 2.5 µm. In some embodiments, the drug-containing polymeric particles have an overall size ranging from about 200 nm to about 800 nm. In some embodiments, the drug-containing polymeric particles have an overall size in the 2-20 nm range and are particularly useful for delivery to cells.

In some embodiments, the drug-containing polymeric particles disclosed herein can be surface-modified to provide functional groups that can be used to link the particles to a binding moiety, e.g., a lymphocyte homing adhesion molecule or an antibody that binds a ligand of the lymphocyte homing adhesion molecule described herein. For example, the particles can be functionalized according to a version of the method of Albrecht et al., Biochimie, 80(5-6): 379-90, 1998. Dimercapto-succinic acid can be coupled to the particles and provides a carboxyl functional group. By functionalized is meant the presence of amino or carboxyl or other reactive groups that can be used to attach desired moieties to the particles.

Carboxyl functionalized nano- or microparticles can be made, for example, according to the method of Gorman (see WO 00/61191). Carboxyl-functionalized particles can also be made from polysaccharide coated particles by reaction with bromo or chloroacetic acid in strong base to attach carboxyl groups. In addition, carboxyl-functionalized particles can be made from amino-functionalized particles by converting amino to carboxyl groups by the use of reagents such as succinic anhydride or maleic anhydride.

Particles can also be treated with periodate to form aldehyde groups. The aldehyde-containing particles can then be reacted with a diamine (e.g., ethylene diamine or hexanediamine), which will form a Schiff base, followed by reduction with sodium borohydride or sodium cyanoborohydride.

Dextran-coated particles can also be made and cross-linked, e.g., with epichlorohydrin. The addition of ammonia will react with epoxy groups to generate amine groups, see Hogemann et al., Bioconjug. Chem. 2000. 11(6):941-6, and Josephson et al., Bioconjug. Chem., 1999, 10(2):186-91.

Carboxyl-functionalized particles can be converted to amino-functionalized magnetic particles by the use of water-soluble carbodiimides and diamines such as ethylene diamine or hexane diamine.

Avidin or streptavidin can be attached to particles for use with a biotinylated binding moiety, such as an oligonucleotide or polypeptide. See e.g., Shen et al., Bioconjug. Chem., 1996, 7(3):311-6. Similarly, biotin can be attached to a particle for use with an avidin-labeled binding moiety.

In some embodiments, the drug-containing polymeric particles can be pegylated, e.g., as described in U.S. Pat. Nos. 7,291,598; 5,145,684; 6,270,806; 7,348,030, and others, to reduce blood protein binding, and/or liver and spleen uptake. Pegylation creates stealth-like structures to bypass immune recognition by macrophage cells, thus achieving suppressed opsonization and enhanced retention of the particles in circulation. Such simple surface modification, e.g., pegylation, can increase the circulation half-life of a particle from several minutes to several or tens of hours.

Lymphocyte Homing Adhesion Molecules and their Ligands

Lymphocytes migrate continuously from blood to various secondary lymphoid organs and extra lymphoid tissues, to lymph and return back to the blood (Michie S A, Am J Pathol 143:1688-1698, 1993). A majority of lymphocytes are capable of tissue selective trafficking, termed "lymphocyte homing." Tissue-specific homing is thought to account for the regional compartmentalization of immune system functions and to control the extent and scope of local immune and inflammatory responses. Homing of leukocytes involves at least three consecutive steps: tethering and rolling mediated by primary adhesion molecules on the luminal wall of postcapillary venules, termed "high endothelial venules" (HEVs); exposure to a chemotactic stimulus provided by chemokines and G-protein—coupled receptors; and arrest mediated by activated integrins (von Andrian, U. H. & Mackay, C. R., N Engl J Med 343, 1020-1034 2000).

Lymphocyte subsets as well as endothelial cells specifically program their expression of adhesion molecules and chemokine/chemokine receptors, allowing lymphocytes to move selectively to specific functional compartments of the immune system. The unique combination of adhesion molecules and chemokine receptors on the cell surface of a lymphocyte is called "homing signature", which enables it to recognize and leave the blood at specialized endothelial "address" sites expressing the relevant ligands, thus allowing tissue-specific homing (Pals S. T., de Gorter D. J. J., and Spaargaren M, Blood 110(9): 3102-3111, 2007).

To target the drug-containing polymeric particles to specific lymphoid tissues and sites of chronic inflammation, the particles disclosed herein can be coated with a lymphocyte homing adhesion molecule, or an antibody that binds a ligand of the lymphocyte homing adhesion molecule expressed on high endothelial venules. Exemplary lymphocyte homing adhesion molecules and their ligands expressed on high endothelial venules are listed in Table 1 (adapted from Pals S. T., de Gorter D. J. J., and Spaargaren M, Blood 110(9): 3102-3111, 2007).

TABLE 1

Lymphocyte Homing Adhesion Molecules and Their Ligands

| Adhesion molecules | Expression on lymphocytes | Ligand | Predominant sites of homing |
|---|---|---|---|
| L-selectin (also known as TQ1; LAM1; LEU8; LNHR; LSEL; CD62L; LYAM1; PLNHR; LECAM1) | Naive T and B cells, Central memory T cells | PNAd (MAdCAM-1) | Peripheral lymph node |
| CLA | Skin homing T cells | E-selectin | Skin |
| α4β7 | Naive T and B cells (low), gut-homing T-cells (high), IgA plasmablasts | MAdCAM-1 (VCAM-1) | Gut |
| αEβ7 | Intraepithelial T cells | E-cadherin | Epithelium |
| αLβ2 (LFA-1) | Broad expression on T and B cells | ICAM-1, ICAM-2 | Multiple sites |
| α4β1 (VLA-4) | Broad expression on T and B cells | VCAM-1 | Inflammatory sites and bone marrow |

VLA: very late antigen;
MAdCAM: mucosal addressin cell adhesion molecule;
VCAM: vascular cell adhesion molecule;
ICAM: intercellular adhesion molecule;
CLA: cutaneous lymphocyte antigen;
ICAM: intercellular adhesion molecule;
LFA: lymphocyte function-associated;
PNAd: peripheral lymph node addressin.

In some embodiments, the drug-containing polymeric particles disclosed herein can be coated with a lymphocyte homing adhesion molecule selected from L-selectin, cutaneous lymphocyte antigen (CLA), α4β7 integrin, αEβ7 integrin, αLβ2 integrin, and α4β1 integrin.

In some embodiments, the drug-containing polymeric particles disclosed herein can be coated with an antibody that binds a ligand of a lymphocyte homing adhesion molecules, e.g., an antibody for PNAd, an antibody for E-selectin, an antibody for MAdCAM-1, an antibody for E-cadherin, an antibody for ICAM-1 or ICAM-2, or antibody for VCAM-1.

In some embodiments, to target the drug-containing polymeric particles disclosed herein to peripheral lymph nodes, the particles can be coated with L-selectin or an antibody that binds PNAd, e.g., MECA-79 or S2 monoclonal antibodies.

In some embodiments, to target drug-containing polymeric particles disclosed herein to skin, the particles can be coated with cutaneous lymphocyte antigen (CLA), or antibody that binds E-selectin.

In some embodiments, to target the drug-containing polymeric particles to gastrointestinal tract, the particles disclosed herein can be coated with α4β7 integrin or an antibody that binds MAdCAM-1.

In some embodiments, to target the drug-containing polymeric particles to epithelium, the particles disclosed herein can be coated with αEβ7 integrin or an antibody that binds E-cadherin.

In some embodiments, to target the drug-containing polymeric particles to bone marrow and inflammatory sites, the particles disclosed herein can be coated with α4β1 integrin or an antibody that binds VCAM-1.

In some embodiments, to target the drug-containing polymeric particles to multiple lymphoid tissues, the particles disclosed herein can be coated with αLβ2 integrin or an antibody that binds ICAM-1 or ICAM-2.

L-Selectin

The selectins are a family of cell-surface glycoproteins responsible for early adhesion events in the recruitment of leukocytes into sites of inflammation and their emigration into lymphatic tissues (Somers, W. S., Tang, J., Shaw, G. D. & Camphausen, R. T., Cell 103: 467-479, 2000). L-selectin is the only selectin expressed on leukocytes that recognizes sulfated sialyl-LewisX (sLeX)-like sugars, called peripheral-node addressin (PNAd) expressed by high endothelial venules (HEVs) in the lymph nodes (von Andrian, U. H. & Mackay, C. R., N Engl J Med 343: 1020-1034, 2000). L-selectin is best known for its role in the initial interaction of lymphocytes with PNAd expressed on HEVs of lymph nodes during the process of lymphocyte homing. The interaction between L-selectin and PNAd plays a key role in the continuous homing of naive T cells to the lymphoid tissues where they encounter antigens presented to antigen-presenting cells. In addition to constitutive lymphocyte trafficking to lymph nodes, L-selectin also plays a key role in the trafficking of leukocytes to the peripheral tissue mediating inflammation through interaction with other ligands on inflamed endothelial cells (Ley, K., et al., J Exp Med 181: 669-675, 1995; Ley, K. & Tedder, T. F., J Immunol 155: 525-528, 1995; Tedder, T. F., Steeber, D. A., Chen, A. & Engel, P., FASEB J 9: 866-873, 1995).

The mRNA and amino acid sequences of mouse, rat and human L-selectin are known in the art and their GeneBank accession numbers are listed in Table 2.

TABLE 2

The mRNA and Amino Acid Sequences of human, mouse, and rat L-selectin

| | mRNA Sequence | Amino Acid Sequences |
|---|---|---|
| Human L-selectin | NM_000655.4 GI: 262206314 | NP_000646.2 GI: 262206315 |
| Mouse L-selectin | NM_011346.2 GI: 255708469 | NP_035476.1 GI: 6755454 |
| Rat L-selectin | NM_019177.3 GI: 94400780 | NP_062050.3 GI: 94400781 |

In some embodiments, the drug-containing polymeric particles disclosed herein are coated with L-selectin to target the particles to peripheral lymph nodes.

Peripheral Lymph Node Addressin (PNAd) and its Antibodies

The peripheral lymph node addressin (PNAd) is a tissue-specific endothelial cell antigen constitutively expressed on HEV in both mouse and human. PNAds are a group of endothelial sialomucins—CD34, podocalixin, glycosylation-dependent cell-adhesion molecule 1 (GlyCAM-1), and sialylated glycoprotein of 200 kDa (sgp200)—all of which include a sulfated sialyl-LewisX (sLeX)-like motif (von Andrian, U. H. & Mackay, C. R., N Engl J Med 343: 1020-1034, 2000). PNAds are expressed on venular endothelium of peripheral lymph nodes, tonsils, almost all the sites of inflammation or lymphomatous lesions, but not in normal tissues of the ocular adnexa, thyroid gland, salivary gland and lung (Liu Y, J Clin Exp Hematopathol 44 (1): 33-37, 2004). PNAds play important roles in lymphocyte homing to the inflamed lesions and in biological behavior of lymphoma cells in MALT lymphoma tissues of these organs.

MECA79 is an IgM monoclonal antibody that recognizes all known L-selectin ligands on endothelial venules—PNAds, including CD34, GlyCAM-1, and a subset of MAdCAM-1 (Hemmerich, S., Butcher, E. C. & Rosen, S. D., J Exp Med 180, 2219-2226, 1994). MECA79 was produced by using collagenase-dispersed mesenteric and peripheral lymph node stromal elements as immunogen and selected based on selective staining of peripheral lymph node HEV. (Streeter et al., J. Cell. Biol. 107:1853-1862, 1988). MECA79 inhibited the binding of normal lymphocytes to peripheral lymph node HEV in vitro, and dramatically reduced the extravasation of normal blood-borne lymphocytes into peripheral lymph nodes in vivo (Streeter et al., 1988). MECA-79 also blocked 38C13, a lymphoma that selectively expresses peripheral lymph node-homing receptors, from binding to peripheral lymph node or to mesenteric lymph node HEV (Streeter et al., 1988). MECA79 has no significant effect on lymphocyte binding to HEV in mucosa-associated lymphoid organs, the Peyer's patches.

MECA79 recognizes a number of human glycoprotein species of distinct molecular weights, with a major tonsil species at 105 kD, a major lymph node component at 200 kD, and several minor species at 65, 90, and 150 kD (Berg, E. L., et al., J Cell Biol 114, 343-349, 1991). In mouse, MECA79 recognizes two predominant glycoproteins of 90 and 115 kD, a minor 65 kD species, and additional species at 50, 75, 170, and 200 kD (Berg, E. L., et al., J Cell Biol 114, 343-349, 1991). The 50 kD glycoprotein was subsequently identified at the molecular level as the secreted glycoprotein GlyCAM-1, and the 90 kD glycoprotein was identified to be a HEV-specific glycoform of the transmembrane glycoprotein CD34 (Hemmerich, S., Butcher, E. C. & Rosen, S. D., J Exp Med 180, 2219-2226, 1994). The molecules around 60 kD were shown to be a subset of MAdCAM-1, a novel glycoprotein possessing both Ig-like domains and a mucin domain (Hemmerich, S., Butcher, E. C. & Rosen, S. D., J Exp Med 180, 2219-2226, 1994).

All these vascular addressins are mucin-like glycoproteins that bear sulfated, sialylated, and fucosylated O-linked carbohydrate chains. The occurrence of a common MECA79 epitope on these glycoproteins suggests that it might represent a carbohydrate posttranslational modification closely associated with the vascular addressins that confer binding activity for L-selectin. It was shown that both L-selectin and MECA79 recognize the same set of [$^3$H] galactose-labeled and [$^{35}$S]SO4-labeled glycoproteins from lymph nodes, and the recognition of the HEV-ligands by MECA79 is dependent on sulfation (Hemmerich, S., Butcher, E. C. & Rosen, S. D., J Exp Med 180, 2219-2226, 1994). Thus MECA-79 recognizes the sulfated oligosaccharide carried by the sialomucins.

An anti-carbohydrate monoclonal antibody S2, which was developed by immunizing sulfotransferase-deficient mice with transfected CHO cells that overexpress the glycan epitopes formed by the glycogenes, specifically recognizes 2,3-sialylated 6-sulfo LacNAc and 6-sulfo sialyl Lewis X structures (Hirakawa, J., et al., J Biol Chem 285: 40864-40878, 2010). The S2 antibody was shown to bind both sulfated N- and sulfated O-glycans in HEVs and block lymphocyte homing (Hirakawa, J., et al., 2010). The S2 antibody binds strongly to glycoprotein species of 200, 170, and 90 kDa, which were probably Sgp200, podocalyxin-like protein, and CD34, respectively; but relatively weakly to a 55-60 kDa glycoprotein likely representing GlyCAM-1 (Hirakawa, J., et al., 2010).

In some embodiments, the drug-containing polymeric particles disclosed herein are coated with an antibody that binds PNAds, e.g., MECA79 or S2 monoclonal antibody, to target the particles to peripheral lymph nodes.

Antibodies Against Lymphocyte Homing Adhesion Molecules or their Ligands

In some embodiments, the drug-containing polymeric particles disclosed herein are conjugated with an antibody that binds a ligand expressed on the high endothelial venules for the lymphocyte homing adhesion molecule. For example, the drug-containing polymeric particles can be conjugated with MECA79, the monoclonal antibody that recognizes all known L-selectin ligands on endothelial venules—PNAds, including CD34, GlyCAM-1, and a subset of MAdCAM-1 (Hemmerich, S., Butcher, E. C. & Rosen, S. D., J Exp Med 180, 2219-2226, 1994). In some embodiments, the drug-containing polymeric particles can be conjugated with the monoclonal antibody S2 developed by Hirakawa (J Biol Chem 285: 40864-40878, 2010).

The term "antibody," as used herein, refers to full-length, two-chain immunoglobulin molecules and antigen-binding portions and fragments thereof. A typical full-length antibody includes two heavy (H) chain variable regions (abbreviated herein as VH), and two light (L) chain variable regions (abbreviated herein as VL). The term "antigen-binding fragment" of an antibody, as used herein, refers to one or more fragments of a full-length antibody that retain the ability to specifically bind to a target. Examples of antigen-binding fragments include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426 (1988); and Huston et al. Proc. Natl.

Acad. Sci. USA 85:5879-5883 (1988)). Such single chain antibodies are also encompassed within the term "antigen-binding fragment."

Production of antibodies and antibody fragments is well documented in the field. See, e.g., Harlow and Lane, 1988. *Antibodies, A Laboratory Manual.* Cold Spring Harbor, N.Y.: Cold Spring Harbor Laboratory. For example, Jones et al., Nature 321: 522-525 (1986), which discloses replacing the CDRs of a human antibody with those from a mouse antibody. Marx, Science 229:455-456 (1985), discusses chimeric antibodies having mouse variable regions and human constant regions. Rodwell, Nature 342:99-100 (1989), discusses lower molecular weight recognition elements derived from antibody CDR information. Clackson, Br. J. Rheumatol. 3052: 36-39 (1991), discusses genetically engineered monoclonal antibodies, including Fv fragment derivatives, single chain antibodies, fusion proteins chimeric antibodies and humanized rodent antibodies. Reichman et al., Nature 332: 323-327 (1988) discloses a human antibody on which rat hypervariable regions have been grafted. Verhoeyen, et al., Science 239: 1534-1536 (1988), teaches grafting of a mouse antigen binding site onto a human antibody.

Methods of Conjugation

The drug-containing polymeric particles described herein are conjugated with a molecule that regulates lymphocyte homing described herein, e.g., a lymphocyte homing adhesion molecule, or an antibody that binds a ligand of the lymphocyte homing adhesion molecule.

The molecule that regulates lymphocyte homing can be linked to the drug-containing polymeric particles through covalent attachment, e.g., through a chemical bond between a functional group on the molecule and a functional group on the drug-containing polymeric particles. A functional group can be an amino or carboxyl or other reactive groups that can be used to attach desired moieties to the particles, e.g., a lymphocyte homing adhesion molecule, or an antibody that binds a ligand of the lymphocyte homing adhesion molecule.

In some embodiments, the molecule that regulates lymphocyte homing can be attached to the drug-containing polymeric particles via a linker or binding agent. The linker or binding agent can have terminal amino, carboxy, sulfhydryl, or phosphate groups. Illustrative examples of useful linkers or binding agents include organic polymers, e.g., polyethylene glycol (PEG) and derivatives thereof, proteins, and small molecules.

Methods of Treatment

As described above, the present disclosure is based, at least in part, on the development of drug-containing polymeric particles that mimic lymphocyte migration in vivo and can specifically deliver immunosuppressive or immunoregulatory drugs to lymphoid tissues and sites of chronic inflammation where T-cell activation and T-cell mediated injury are occurring. Accordingly, the present disclosure provides compositions and methods for treating, or delaying disease progression in a subject (e.g., a human) in need of immune suppression, e.g., for autoimmune or inflammatory disorders such as type 1 diabetes or rheumatoid arthritis; and immune suppression following transplantation, e.g., in cardiac or other organ transplantation. The present disclosure also provides methods of treating, or delaying progression of malignancies, such as lymphomas, where the lymphocyte homing process plays a role in the dissemination of the tumor, and/or wherein the malignancy expresses PNAd by delivering chemotherapy drugs to lymphoid tissues. These methods can include identifying a subject in need of treatment and administering to the subject one or more of the compositions described herein. A subject in need of treatment can be identified, e.g., by a medical practitioner.

Methods of Treating Autoimmune Diabetes

Type 1 diabetes (T1D) is characterized by the autoimmune destruction of insulin-producing β cells of the pancreatic islets by autoreactive T cells (Hoglund, P., et al., J Exp Med 189: 331-339, 1999). Central to the pathogenesis of autoimmune diabetes is the presentation of islet antigens by antigen-presenting cells in the draining pancreatic lymph nodes to T cells, resulting in the activation of autoreactive T cells (Roncarolo, M. G. & Battaglia, M., Nat Rev Immunol 7: 585-598, 2007). A number of studies indicate the pancreatic lymph nodes play critical roles in the pathogenesis of autoimmune diabetes (Katz, J. D., Wang, B., Haskins, K., Benoist, C. & Mathis, D. Cell 74: 1089-1100, 1993; Hoglund, P., et al., J Exp Med 189, 331-339, 1999; Turley, S., Poirot, L., Hattori, M., Benoist, C. & Mathis, D., J Exp Med 198: 1527-1537, 2003; Turley, S. J., Lee, J. W., Dutton-Swain, N., Mathis, D. & Benoist, C., Proc Natl Acad Sci USA 102: 17729-17733, 2005). Following priming, activated autoreactive T cells are then recruited to the pancreas causing insulitis.

The L-selectin/PNAd pathway has been shown to regulate lymphocyte trafficking to lymphoid tissue in NOD mice (Hanninen, A., Salmi, M., Simell, O., Andrew, D. & Jalkanen, S., Blood 88: 934-944, 1996; Xu, B., et al., J Exp Med 197: 1255-1267, 2003; Xu, B., Cook, R. E. & Michie, S. A., J Autoimmun. 35: 124-129, 2010). Moreover, PNAd is upregulated on venous endothelium in inflammatory states and autoimmune diseases such as T1D (Michie, S. A., Streeter, P. R., Bolt, P. A., Butcher, E. C. & Picker, L. J., Am J Pathol 143: 1688-1698, 1993; Mikulowska-Mennis, A., Xu, B., Berberian, J. M. & Michie, S. A., Am J Pathol 159: 671-681, 2001; Penaranda, C. & Bluestone, J. A., Immunity 31: 534-536, 2009). Inflammatory signals and endothelial cell activation during insulitis have been reported to render islet endothelial morphology and characteristics to HEVs expressing PNAd. Therefore, the onset of insulitis is reported to be associated with islet expression of PNAd (Hanninen, A., Salmi, M., Simell, O., Andrew, D. & Jalkanen, S., Blood 88, 934-944, 1996; Faveeuw, C., Gagnerault, M. C., Kraal, G. & Lepault, F., Int Immunol 7: 1905-1913, 1995; Yang, X. D., et al., Proc Natl Acad Sci USA 91: 12604-12608, 1994; Yang, X. D., et al., J Autoimmun 7: 859-864, 1994; Faveeuw, C., Gagnerault, M. C. & Lepault, F., J Immunol 152: 5969-5978, 1994; Hanninen, A., Salmi, M., Simell, O. & Jalkanen, S., Diabetes 45: 1173-1180, 1996; Dong, H., Burke, S. D. & Croy, B. A., Placenta 29: 201-209, 2008). The interaction of leukocytes with endothelial cells via adhesion molecules affords great opportunity to design various strategies such as developing inhibitors or antibodies that target the trafficking of leukocytes (Mackay, C. R., Nat Immunol 9: 988-998, 2008).

The particles conjugated with a molecule that regulates lymphocyte homing described herein can be used to selectively deliver immunosuppressant to the pancreatic lymph nodes and pancreas to efficiently suppress autoreactive T cells and to treat or delay progression of autoimmune diabetes such as type 1 diabetes (T1D). A subject who has some pancreatic β cell function is more likely to benefit from the present method of treatment. Such a subject can be identified, e.g., by determining the C-peptide level in the subject is above a threshold.

Immune Suppression after Transplantation

After tissue or organ transplantation, immune cells are activated against exogenous antigens present on the allografts. The activated immune cells can travel to the transplanted tissue or organ and cause damages there. Delivery of a small amount of immunosuppressive drugs directly to the sites where immune cells are activated can reduce their activation and increase allograft survival. Such targeted delivery of immunosuppressive drugs also reduces toxicity seen in systemic administration of a large amount of immunosuppressive medications. The compositions described herein are useful vehicles to deliver immunosuppressant directly to the sites of organ transplantation and increase allograft survival.

Methods of Treating Lymphomas

The compositions described herein can also be used to treat lymphomas, e.g., PNAd-expressing lymphomas. Lymphocyte homing process is known to play a role in the dissemination of some tumors. For example, the dissemination of non-Hodgkin lymphomas (NHLs) is mediated by lymphocyte homing program (Pals S. T., de Gorter D. J. J., and Spaargaren M, Blood 110(9): 3102-3111, 2007). Other exemplary lymphomas that can be treated by the compositions disclosed herein include small-lymphocytic lymphoma (SLL), chronic lymphocytic leukemia (CLL), mantle-cell lymphoma (MCL), Burkitt lymphoma (BL), diffuse large B-cell lymphomas (DLBCL), cutaneous lymphomas, e.g., cutaneous T cell lymphoma (CTCL), intestinal lymphomas, e.g., intestinal T-cell lymphomas (ITLs), nodal T-cell lymphomas, extranodal lymphomas arising in the gut-associated lymphoid tissues or the skin, adult T-cell leukemia/lymphoma (ATLL), and B-cell lymphomas of the mucosa-associated lymphoid tissues (MALTs), primary follicular lymphomas (FLs), B-cell chronic lymphocytic leukemia (B-CLL), and hairy-cell leukemia (HCL).

In some embodiments, the particles conjugated with L-selectin or an antibody that binds PNAd described herein can be used to treat or delay progression of PNAd-expressing lymphomas.

Pharmaceutical Formulations

A therapeutically effective amount of one or more of the compositions described herein can be incorporated into pharmaceutical compositions suitable for administration to a subject, e.g., a human. Such compositions typically include the composition and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions, e.g., an inhibitor of degradation of the ligand.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (polyethoxylated castor oil; BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™ (sodium carboxymethyl starch), or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration. In one aspect, the pharmaceutical compositions can be included as a part of a kit.

Generally the dosage used to administer a pharmaceutical composition facilitates an intended purpose for prophylaxis and/or treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: "Remington's Pharmaceutical Sciences", 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

Administration

A therapeutically effective amount of one or more of the compositions described herein can be administered by standard methods, for example, by one or more routes of administration, e.g., by one or more of the routes of administration currently approved by the United States Food and Drug Administration (FDA; see, for example world wide web address fda.gov/cder/dsm/DRG/drg00301.htm), e.g., orally, topically, mucosally, or parenterally, e.g., intravenously or intramuscularly.

Kits

The present invention also includes kits for use in a method described herein. In some embodiments the kits comprise one or more doses of a composition described herein. The composition, shape, and type of dosage form for the induction regimen and maintenance regimen may vary depending on a subject's requirements. For example, dosage form may be a parenteral dosage form, an oral dosage form, a delayed or controlled release dosage form, a topical, and a mucosal dosage form, including any combination thereof.

In a particular embodiment, a kit can contain one or more of the following in a package or container: (1) one or more doses of a composition described herein; (2) one or more pharmaceutically acceptable adjuvants or excipients (e.g., a pharmaceutically acceptable salt, solvate, hydrate, stereoisomer, or clathrate); (3) one or more vehicles for administration of the dose; (5) instructions for administration. Embodiments in which two or more, including all, of the components (1)-(5), are found in the same container can also be used.

When a kit is supplied, the different components of the compositions included can be packaged in separate containers and admixed immediately before use. Such packaging of the components separately can permit long term storage without loosing the active components' functions. When more than one bioactive agent is included in a particular kit, the bioactive agents may be (1) packaged separately and admixed separately with appropriate (similar of different, but compatible) adjuvants or excipients immediately before use, (2) packaged together and admixed together immediately before use, or (3) packaged separately and admixed together immediately before use. If the chosen compounds will remain stable after admixing, the compounds may be admixed at a time before use other than immediately before use, including, for example, minutes, hours, days, months, years, and at the time of manufacture.

The compositions included in particular kits of the present invention can be supplied in containers of any sort such that the life of the different components are optimally preserved and are not adsorbed or altered by the materials of the container. Suitable materials for these containers may include, for example, glass, organic polymers (e.g., polycarbonate and polystyrene), ceramic, metal (e.g., aluminum), an alloy, or any other material typically employed to hold similar reagents. Exemplary containers can include, without limitation, test tubes, vials, flasks, bottles, syringes, and the like.

As stated above, the kits can also be supplied with instructional materials. These instructions may be printed and/or may be supplied, without limitation, as an electronic-readable medium, such as a floppy disc, a CD-ROM, a DVD, a Zip disc, a video cassette, an audiotape, and a flash memory device. Alternatively, instructions may be published on an internet web site or may be distributed to the user as an electronic mail.

EXAMPLES

The invention is further described in the following examples, which do not limit the scope of the invention described in the claims.

Example 1

Synthesis and Characterization of TAC-PLA-MECA79 Microparticles

FIG. 1 illustrates an exemplary process for synthesizing TAC-PLA-MECA79 microparticles. TACROLIMUS (TAC) was used to initiate lactide polymerization in the presence of Zn catalysts. Briefly, TAC was mixed with an equivalent amount of the active catalyst $(BDI)ZnN(TMS)_2$, followed by the addition of lactide. (BDI)Zn-TAC (FK506) complex, formed in situ, initiated and completed the polymerization of lactide at room temperature within 12 hours (FIG. 1a). The loading of TAC was examined by matrix-assisted laser desorption ionization imaging mass spectrometry (MALDI).

MALDI results showed that the TAC-polylactide (TAC-PLA) fragment has the expected drug end group and the intended chemical structure of TAC-PLA conjugate (FIG. 2a). Gram-scale TAC-PLA polymer with a well-controlled composition and drug loading can be prepared using this drug-initiated polymerization method.

To further stabilize the TAC-PLA nanoconjugates with a larger inert surface (to reduce immunogenicity), the TAC-PLA were PEGylated. TAC-PLA was mixed with PLA-PEG-COOH to synthesize TAC-PLA/PLA-PEG-COOH nanoconjugates through double emulsion methods. The surface carboxylate group can be used for the conjugation of antibody through coupling chemistry (FIG. 1) (Tong, R. & Cheng, J., Angew. Chem., Int. Ed. 47, 4830-4834 2008; Chamberlain, B. M., J. Am. Chem. Soc. 123, 3229-3238, 2001). The formed microparticles with carboxyl groups were further conjugated with protein G by a coupling reaction and then bonded with MECA79 (FIG. 1b).

The sizes of the nanoconjugates were determined by a dynamic light scattering (DLS) detector; the resulting microparticles were about 2.30±0.14 μm in diameter (FIG. 2b), which is the typical size for particles prepared through double emulsion methods. The scanning electron microscopy (SEM) image also showed that the microparticles are about 2 μm in size (FIG. 2c, the image of the dried microparticle sample).

Example 2

The Immunosuppressive Effects of TAC-PLA-MECA79 Microparticles

To examine the retaining and releasing capacity of TAC from the TAC-PLA-MECA79 microparticles, the immunosuppressive capacity of the microparticle to suppress T cell proliferation was tested. TAC-PLA-MECA79 microparticles were added in a dose-dependent fashion to a mixed leukocyte reaction (MLR). Briefly, in each well of a 96-well round plate, $5 \times 10^5$ splenocytes from C57BL/6 mice were added to $5 \times 10^5$ irradiated BALB/c (fully mismatched) splenocytes. Various amounts of TAC-PLA-MECA79 microparticles were then added to the wells based on an increasing concentration of incorporated TAC. T cell proliferation was measured 72 hours later by $^3$H thymidine incorporation. As shown in FIG. 3, when compared to positive control (PC), TAC-PLA-MECA79 microparticles suppressed T cell proliferation in a dose-dependent fashion (*$p<0.05$).

Example 3

Selective Delivery of MECA79-Coated Microparticles to Pancreatic Lymph Nodes

The priming and activation of autoreactive T cells occurs in the pancreatic lymph nodes, from where the activated T cells traffic to the pancreas to target islets (Katz, J. D., Wang, B., Haskins, K., Benoist, C. & Mathis, D. Cell 74: 1089-1100, 1993; Hoglund, P., J Exp Med 189: 331-339, 1999; Turley, S., Poirot, L., Hattori, M., Benoist, C. & Mathis, D. J Exp Med 198: 1527-1537, 2003; Turley, S. J., Lee, J. W., Dutton-Swain, N., Mathis, D. & Benoist, C. Proc. Natl. Acad. Sci. USA 102: 17729-17733, 2005; Clare-Salzler, M. & Mullen, Y. Immunology 76:478-484, 1992; Fabien, N., Bergerot, I., Maguer-Satta, V., Orgiazzi, J. & Thivolet, C., J Autoimmun 8: 323-334, 1995; Alam, C., Valkonen, S., Ohls, S., Tornqvist, K. & Hanninen, A., Diabetologia 53: 346-355, 2010; Nti, B. K., Cell Mol Immunol 9, 455-463, 2012).

Figure 4A:
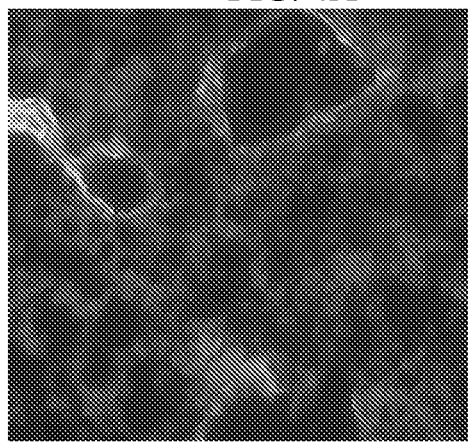
FIGS. 4A and 4B are immunohistochemistry images showing higher expression level of PNAd in pancreatic lymph nodes (PLN, 4A) than in inguinal lymph nodes (4B). Medium grey (blue in original) represents DAPI staining; light grey (green in original) color represents PNAd staining.
Figure 4B:
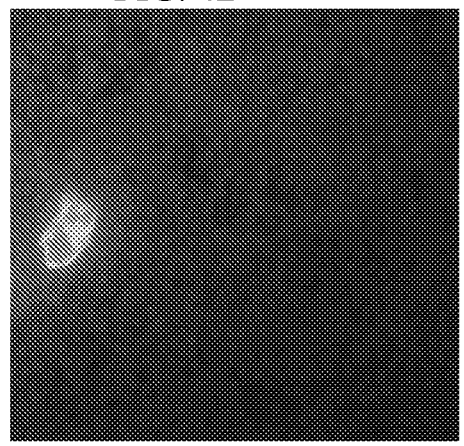

The level of PNAd expression in the pancreatic lymph nodes (PLN) and inguinal lymph nodes of non-obese diabetic (NOD) mice was examined. Lymph nodes were sectioned and stained for PNAd. As shown in FIGS. 4A and 4B, PNAd was more extensively expressed in PLN, notably on the extensive small mesh-like structures extended out from the PNAd-expressing vessels (FIG. 4A), as compared to the inguinal lymph nodes (FIG. 4B).

Figure 5A:
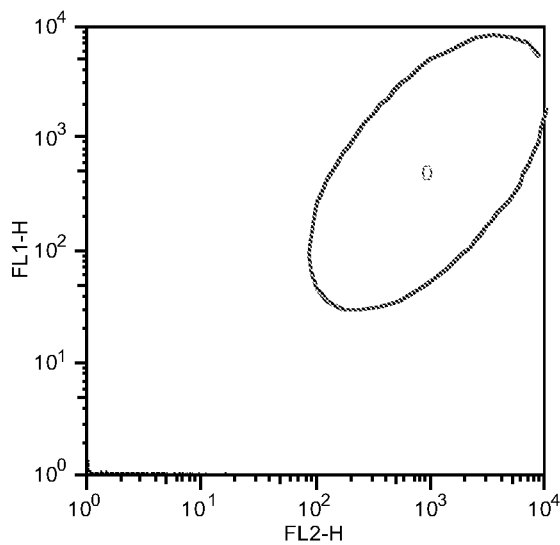
FIGS. 5A and 5B are flow cytometry graphs showing selective delivery of MECA79-coated particles to pancreatic lymph node (5B) as compared to the uncoated particles without the MECA79 antibody (5A) in twelve-week old non-obese diabetic (NOD) mice.
Figure 5B:
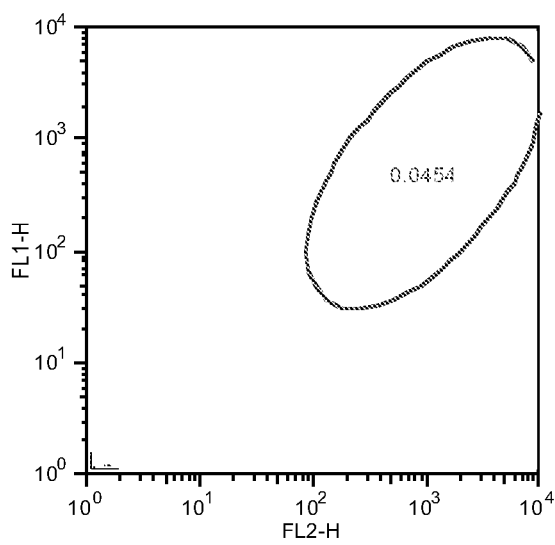
Figure 6A:
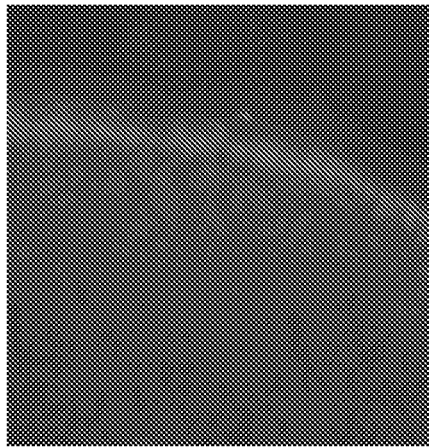
FIGS. 6A and 6B are immunohistochemistry images showing selective delivery of rhodamine-labeled MECA79-coated particles to pancreatic lymph nodes (6B) as compared to inguinal lymph nodes (6A). Medium grey areas (blue in original images) represented DAPI staining; lighter grey (red in original images) represented the rhodamine-labeled particles.
Figure 6B:
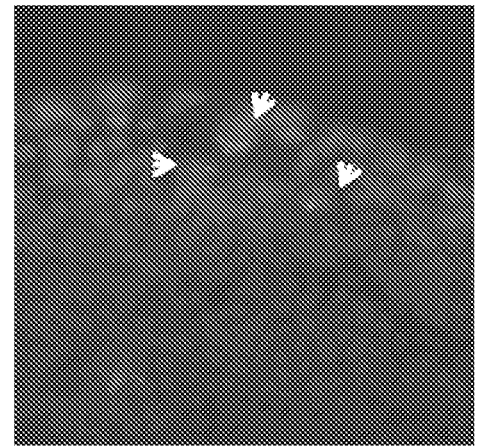

The efficacy of MECA79-coated microparticles in forcing the trafficking of the attached drugs specifically to the sites of T cell activation and injury was examined in diabetic mice. The actual delivery of particles to specific sites following systemic administration is an undeveloped area of nanomedicine. Rhodamine-containing microparticles were synthesized to enable tracking the particles by techniques such as flow cytometry. Twelve-week old non-obese diabetic (NOD) mice were injected intravenously with either MECA79-coated rhodamine particles or with uncoated rhodamine particles. Pancreatic lymph nodes were removed from these mice 24 hours after the injection. Cells were isolated from the pancreatic lymph node and subjected to flow cytometry. As shown in FIGS. 5A and 5B, pancreatic lymph node cells isolated from mice injected with uncoated rhodamine particles contain virtually no particles (FIG. 5A); pancreatic lymph node cells isolated from mice injected with MECA79-coated rhodamine particles demonstrated significant trafficking of the particles to the pancreatic lymph node (FIG. 5B). The trafficking of rhodamine-labeled MECA79-coated particles to PLN and inguinal lymph node were examined by immunohistochemistry. As shown in FIGS. 6A and 6B, more MECA-79 coated particles (white arrowheads) were present in the PLN (FIG. 6B) than in the inguinal lymph nodes (FIG. 6A), showing selective delivery of rhodamine-labeled MECA79-coated particles to PLN.

Similar trafficking studies were also performed in three-week old NOD mice. Interestingly, a high number of MECA79-coated particles (bright medium grey speckles, red in original) trafficked to PLN in this age group of NOD mice, which typically do not show much inflammation in the pancreas (FIG. 7). These data highlight the potential of using the drug delivery system described herein in the prevention as well as the treatment of type 1 diabetes (T1D).

To examine the trafficking of MECA79-coated particles to pancreas, NOD mice were injected with rhodamine-labeled MECA79-coated particles and the pancreas of these NOD mice were stained. As shown in the FIGS. 8A-8C, increased trafficking of MECA79-coated rhodamine-labeled particles was observed in the peri-islet area (FIG. 8A). Further examination of the expression of PNAd and insulin revealed the accumulation of MECA79-coated particles around PNAd-expressing peri-islet vasculatures that surround the insulin-expressing islets (white line) outlined by dense lymphocytes (grey line) (FIG. 8B). Focusing on the PNAd-expressing vasculature further revealed that MECA79-coated particles (small arrows) were located within the vicinity of PNAd-expressing peri-islet microvasculature (large arrows) (FIG. 8C).

To our knowledge, this is the first report of pancreatic lymph node-specific nanomedicine-based delivery technology with demonstrated in vivo efficacy.

Example 4

Selective Delivery of MECA79-Coated Particles to Draining Lymph Nodes in the Transplant Setting To further explore the capability of MECA79-based platform in selectively delivering drugs to specific lymphatic loci where T cell activation is taking place, skin transplants having distinct lymphatic drainage were utilized for the ease of imaging and recovery of lymph nodes for trafficking studies. Full thickness skin grafts were taken from the lateral thoracic skin of the C57BL/6 donor and engrafted onto the BALB/c recipients' lumbar region as described previously (Yuan, X., et al., J Immunol 170: 2949-2955, 2003). Seven days after transplantation, recipient mice were injected with either MECA79-coated rhodamine particles or uncoated particles via the tail vein. Inguinal draining lymph nodes were harvested 24 hours after injection. Lymph node sections were stained for PNAd (green in original images) and counterstained with DAPI (blue in original images) for nuclei. These sections were examined for the presence of rhodamine MECA79-particles (red in original images). As shown in FIGS. 9A and 9B, a much higher number of red particles (9A) were found in the draining lymph nodes of mice injected with MECA79-coated particles as compared to that in mice injected with uncoated particles (9B). Live imaging also indicated an enhanced selective trafficking of TAC-MECA79 microparticles to draining lymph nodes following transplantation.

Example 5

PNAd Blockade Abrogates the Selective Trafficking of MECA79-Coated Microparticles Selectin dependency in the selective recruitment of MECA79-coated particles was then tested by using anti-PNAd antibody. Briefly, BALB/c mice were transplanted with fully mismatched C57BL/6 skin. Seven days after transplantation, these transplant recipients were treated with anti-PNAd antibody or vehicle intravenously as previously described (Rosen, S. D., Tsay, D., Singer, M. S., Hemmerich, S. & Abraham, W. M., Am J Pathol 166: 935-944, 2005). One hour following treatment, mice were injected intravenously with either MECA79-coated microparticles or uncoated microparticles. Draining inguinal lymph nodes were recovered 24 hours later; and cells were isolated from these lymph nodes and subjected to flow cytometry analysis. As shown in FIGS. 10A and 10B, cells from the inguinal lymph nodes of mice injected with anti-PNAd antibody followed by intravenous injection with MECA79-coated microparticles showed a significant decrease in the percentage and absolute count of trafficked microparticles (10B) when compared to mice injected only with MECA79-coated microparticles (10A, 185.8±57.95 vs. 1527±480.8 respectively, p=0.01, n=3 mice/group). Furthermore, the absolute count of the microparticles delivered to the draining lymph nodes was significantly lower in mice injected with anti-PNAd antibody when compared to mice injected with MECA79-coated microparticles (98.33±97.50 vs. 1527±480.8 respectively, p<0.01, n=3 mice/group). However, there was no difference in the absolute count of the microparticles in mice injected with MECA79-coated microparticles compared to mice injected with uncoated microparticles (140.3±67.59 vs. 98.33±97.50 respectively, p=0.6, n=3 mice/group).

Example 6

TAC-MECA79 Microparticles Prolong Heart Allograft Survival in Mice

Figure 11:
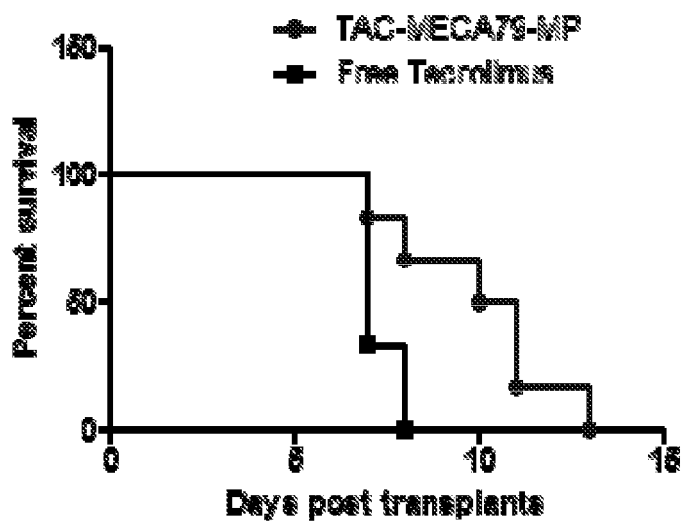
FIG. 11 is a line graph showing that TAC-MP-MECA79 particles significantly prolong heart allograft survival.

Heart allografts from BALB/c donors were transplanted across MHC mismatch mice into C57BL/6 recipients. The recipient mice were then intravenously injected with free Tacrolimus or TAC-MECA79 microparticles. The efficacy of TAC-MECA79 microparticles in promoting heart allograft survival was examined. As compared to mice treated with free Tacrolimus, treating the recipients of heart allografts with TAC-MECA79 microparticles increased heart allograft survival as shown in FIG. 11.

Example 7

Visualization of Delivered Drugs

Figure 12:
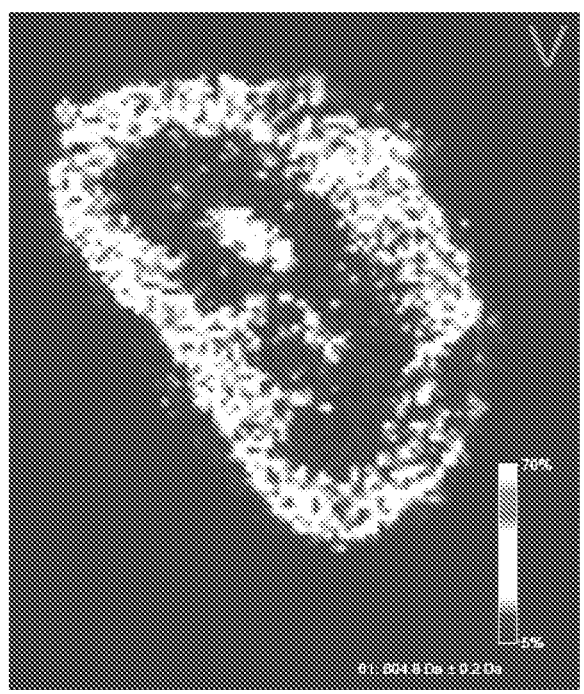
FIG. 12 is a MALDI image showing the intra-kidney distribution of TAC. In the original, the blue signal was the lowest intensity and the red signal was the highest intensity; in the greyscale image, brightness generally correlates with intensity. A large amount of TAC was noted in the cortical areas of the kidney.

Matrix-assisted laser desorption ionization imaging mass spectrometry (MALDI) is used to assess the tissue distribution of delivered drugs. While Example 3 illustrates the efficacy of MECA79-based system in delivering rhodamine microparticles to the pancreatic lymph node, sophisticated tools are needed to properly assess the trafficking of immunoregulatory agents (e.g., TAC) to the target tissue. By using a laser beam to ionize molecules in situ, MALDI can map a wide range of biomolecules in tissues. Optimization of the MALDI technique for detecting TAC in tissue was under the way. Mice were intravenously injected with TAC-PLA-MECA79 microparticles. 24 hours following the injection, kidney was harvested from these mice and examined since kidney is a potential site for TAC accumulation. Cryostat kidney sections were subjected to the MALDI imaging by taking 1,000 laser shots. The selected mass range for the normalized data was 804.8+/−0.2 m/z. FIG. 12 shows a large amount of TAC was noted in the cortical areas of the kidney.

Example 8

The Efficacy of TAC-MECA79 Microparticle Targeted Delivery System in Treating T1D in NOD Mice The efficacy of intravenously injected TAC-MECA79 microparticles in treating T1D in NOD mice is examined. The NOD mice are injected with TAC-MECA79 microparticles or other control agents, and their survival is compared with that of the untreated control mice following previously reported procedures of detecting and monitoring diabetes (Fiorina, P., J Immunol 183: 993-1004, 2009; Jurewicz, M., Diabetes 59: 3139-3147, 2010). Briefly, female NOD mice are monitored closely (5 times/week) for the onset of diabetes (indicated by 2 consecutive days of blood glucose measurements >250 mg/dl) beginning at 10 weeks of age. A relapse of disease in treated animals is evaluated by the same indices. After a second consecutive hyperglycemic measurement (>250 mg/dl) within 24 hours, NOD mice are intravenously injected with TAC-MECA79 microparticles or a control agent such as free TAC, TAC particles, or MECA79 particles.

Although 2.5 mg/kg/day of TAC every other day was shown to efficiently suppress T1D (Kurasawa, K., et al. Clin Immunol Immunopathol 57: 274-279, 1990; Shapiro, A. M., Suarez-Pinzon, W. L., Power, R. & Rabinovitch, A. Diabetologia 45: 224-230, 2002; Kai, N., Motojima, K., Tsunoda, T. & Kanematsu, T., Transplantation 55: 936-940, 1993), variations in the penetrance of autoimmune diabetes in various NOD colonies are possible. Thus, a suboptimal dose of TAC is first determined. Diabetic NOD mice are grouped into three groups and treated with (1) 0.25 mg/kg, (2) 1 mg/kg, or (3) 2.5 mg/kg of TAC every other day for two weeks and the rate of reversal are assessed as described. The degree of reversal of diabetes in NOD mice varies according to the amount of immunosuppression (i.e., dosage of TAC) and the level of hyperglycemia at the onset of diabetes (Bresson, D., J Clin Invest 116: 1371-1381, 2006; Sherry, N. A., Endocrinology 148: 5136-5144, 2007; Valle, A., Diabetes 58: 875-881, 2009). Following identification of reversal groups, the lowest amount of TAC shown to have some degree of efficacy in reversing autoimmune diabetes (i.e. <30% reversal) is selected.

To identify the protective immunoregulatory mechanisms against autoimmune diabetes, a subset of treated and untreated NOD mice are sacrificed at week one and thereafter (according to the duration of diabetes reversal) for the measurement of circulating CD4+ and CD8+ T cells and regulatory and inflammatory cytokines in peripheral blood using 21-plex cytokine kit. The effect of TAC-MECA79 microparticles on Th1/Th2/Th17/IL-6 cytokine production is examined following co-culture of splenocytes with BDC2.5 mimetope as previously described (Fiorina, P., J Immunol 183: 993-1004, 2009; Jurewicz, M., Diabetes 59: 3139-3147, 2010). Cells are isolated from the spleen and the pancreatic lymph node of the TAC-MECA79 treated and untreated mice. FoxP3 Tregs, $CD62^{low}/CD44^{high}$ T cells (effector T cells), and other regulatory immune cells (B regulatory cells and plasmacytoid dendritic cells) are enumerated. Pancreas are recovered and examined for insulitis score, insulin/glucagon staining, and staining for CD3, B cells and FoxP3 Treg infiltration (Tong, R., Yala, L. D., Fan, T. M. & Cheng, J. J. Biomaterials 31: 3043-3053, 2010; Tong, R. & Cheng, J. Polymer Reviews 47: 345-381, 2007).

To examine the site-specific trafficking of the particles and immunoregulatory agents, serum is collected at different time points, TAC level is measured at Biomarker Research/ TIMI Clinical Trials Laboratory. The pancreatic lymph node, spleen, kidney, liver, and pancreas are recovered from treated NOD mice; their histological sections are examined to assess the distribution of TAC release in these organs using MALDI and corroborated with conventional mass spectrometry of digested tissues. Alternatively, TAC is radiolabeled and injected to mice, which are imaged for tracking of the radiolabeled TAC molecules.

Example 9

The Efficacy of Insulin-MECA79 Microparticles in Optimizing Antigen-Specific Immune Therapy Studies using β-cell autoantigens, most notably insulin, have been shown to increase regulatory T cells and regulatory cytokines secretion, and down-regulate effector pathogenic T cells (Polanski, M., Melican, N. S., Zhang, J. & Weiner, H. L., J Autoimmun. 10: 339-346, 1997; Peakman, M. & von Herrath, M., Diabetes 59: 2087-2093, 2010; Kearney, E. R., Pape, K. A., Loh, D. Y. & Jenkins, M. K. Immunity 1: 327-339, 1994; Zhang, Z. J., Davidson, L., Eisenbarth, G. & Weiner, H. L., Proc Natl Acad Sci USA 88: 10252-10256, 1991; Bergerot, I., Diabetes 48: 1720-1729, 1999; von Herrath, M. G., Dyrberg, T. & Oldstone, M. B., J Clin Invest 98: 1324-1331, 1996). While antigen-specific immune therapy (ASI) has garnered much interest as a means of suppressing autoimmunity by inducing β-specific tolerance without the attendant complications of conventional immunosuppressive agents, there is still a need to establish new strategies to further enhance the tolerogenic effect of ASI (Matthews, J. B., Staeva, T. P., Bernstein, P. L., Peakman, M. & von Herrath, M., Clin. Exp. Immunol. 160: 176-184, 2010). One of the key tasks has been to improve the targeted delivery of antigen to specific sites in the body (Takiishi, T., J Clin Invest 122, 1717-1725, 2012). The use of immune cells such as antigen-presenting cells to carry antigen loads is another alternative, but faces limitations including the risk of sensitization and feasibility issues (Florescu, A., Amir, E., Bouganim, N. & Clemons, M., Curr Oncol 18: e9-e18, 2011; Tiwari, M., J Cancer Res Ther 6: 427-431, 2010; Gavalas, N. G., Karadimou, A., Dimopoulos, M. A. & Bamias, A., Clinical & developmental immunology 2010: 791603, 2010).

The targeted nanodelivery system presented herein has the potential to improve the therapeutic efficacy of ASI by improving the trafficking of autoantigen to the sites of T cell priming. Insulin can be incorporated into the MECA79-coated microparticles, which can release insulin over a long period of time.

Insulin-loaded polylactide microparticles displaying MECA79 were prepared using the double emulsion methods following previously reported procedures (Cheng, J., Pharm Res. 23: 557-564, 2006; Teply, B. A., Biomaterials 29: 1216-1223, 2008). The particles were prepared, washed extensively to remove surface-bound insulin, and lyophilized in the presence of lyoprotectant albumin. $I^{125}$-labelled insulin was used to load the microparticles and the loading efficiency was determined based on radioactivity. An ELISA kit was used to analyze the encapsulation and insulin release activity. The final construct is subject to a number of experiments to ensure insulin activity, targeting efficiency and stability in the serum.

The efficacy of the microparticles in enhancing the delivery of insulin to the pancreatic lymph node and pancreas was tested. Briefly, Insulin $I^{125}$-MECA79 microparticles were intravenously injected to newly diabetic NOD mice twice a week via the tail vein. Control NOD mice were injected with controls (e.g., insulin alone, or unloaded control particles). Since the use of 0.5 U/kg of Humulin R (human insulin) in a previous study did not result in significant hypoglycemia (Cheng, J. J., Pharm. Res. 23: 557-564, 2006), titration of insulin is performed with close glucose monitoring to avoid hypoglycemia. The level of delivered insulin in mice was measured as previously described (Cheng, J. J., Pharm. Res. 23: 557-564, 2006). Based on the titration studies with free insulin, various dosages of Insulin $I^{125}$-MECA79 microparticles are chosen for injection. Following the injection, pancreatic lymph node, pancreas and spleen are collected at different time points and examined for the presence of radioactively-labeled insulin using tissue radiolabeled tracer.

Following the identification of the optimal dosage that results in the trafficking of exogenous insulin to the pancreatic lymph node and pancreas, classical reversal studies are carried out. The reversal rate and survival are analyzed and compared as described above. Ex vivo experiments are performed to delineate the status of Tregs, auto-reactive and auto-aggressive T cells and Th1/Th2/Th17 cytokines as described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising one or more drug-containing polymeric particles, each covalently attached to the MECA79 IgM antibody, wherein the polymer comprises poly(lactic-co-glycolic) acid, polylactide, or polyglycolide, and wherein the one or more drug-containing polymeric particles further comprise an anti-CD3 antibody or tacrolimus.

2. The composition of claim 1, wherein the drug-containing polymeric particles are each attached to a MECA79 IgM antibody via a linker comprising polyethylene glycol.

3. The composition of claim 1, further comprising a pharmaceutically acceptable carrier.

4. The composition of claim 1, wherein the MECA79 IgM antibody is humanized or chimeric.

5. The composition of claim 1, wherein the drug-containing polymeric particles comprise an anti-CD3 antibody.

6. The composition of claim 1, wherein the drug-containing polymeric particles comprise tacrolimus.

7. A method of delivering tacrolimus or an anti-CD3 antibody to a subject, the method comprising administering the composition of claim 1 to the subject.

* * * * *

UNITED STATES PATENT AND TRADEMARK OFFICE
CERTIFICATE OF CORRECTION

PATENT NO. : 10,898,581 B2  
APPLICATION NO. : 15/111563  
DATED : January 26, 2021  
INVENTOR(S) : Reza Abdi Page 1 of 1

It is certified that error appears in the above-identified patent and that said Letters Patent is hereby corrected as shown below:

On the Title Page

Column 2 (Other Publications), Line 16, delete "lymp" and insert -- lymph --

In the Specification

In Column 1, Line 10 (approx.), after "foregoing" insert -- applications --

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*